US 7,910,545 B2

(12) United States Patent
Meeker et al.

(10) Patent No.: US 7,910,545 B2
(45) Date of Patent: Mar. 22, 2011

(54) COMBINATION ENZYME REPLACEMENT AND SMALL MOLECULE THERAPY FOR TREATMENT OF LYSOSOMAL STORAGE DISEASES

(75) Inventors: David Meeker, Lincoln, MA (US); Seng H. Cheng, Wellesley, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 11/762,689

(22) Filed: Jun. 13, 2007

(65) Prior Publication Data

US 2007/0280925 A1    Dec. 6, 2007

Related U.S. Application Data

(62) Division of application No. 09/884,526, filed on Jun. 19, 2001, now abandoned.

(60) Provisional application No. 60/212,377, filed on Jun. 19, 2000.

(51) Int. Cl.
*A01N 37/18* (2006.01)
*A01N 61/00* (2006.01)
*C07K 1/00* (2006.01)

(52) U.S. Cl. .................. 514/2; 514/1; 530/350

(58) Field of Classification Search .............. 514/1, 2; 530/350
See application file for complete search history.

(56) References Cited

U.S. PATENT DOCUMENTS

| 5,236,838 | A |   | 8/1993  | Rasmussen et al. |
|-----------|---|---|---------|------------------|
| 5,272,071 | A |   | 12/1993 | Chappel |
| 5,549,892 | A |   | 8/1996  | Friedman et al. |
| 5,650,096 | A |   | 7/1997  | Harris et al. |
| 5,658,567 | A | * | 8/1997  | Calhoun et al. ............ 424/94.61 |
| 5,670,488 | A |   | 9/1997  | Gregory et al. |
| 5,707,618 | A |   | 1/1998  | Armentano et al. |
| 5,719,131 | A |   | 2/1998  | Harris et al. |
| 5,747,471 | A |   | 5/1998  | Siegel et al. |
| 5,756,283 | A |   | 5/1998  | Wilson et al. |
| 5,767,099 | A |   | 6/1998  | Harris et al. |
| 5,783,565 | A |   | 7/1998  | Lee et al. |
| 5,824,544 | A |   | 10/1998 | Armentano et al. |
| 5,827,703 | A |   | 10/1998 | Debs et al. |
| 5,836,905 | A |   | 11/1998 | Lemelson et al. |
| 5,840,702 | A |   | 11/1998 | Bedwell |
| 5,840,710 | A |   | 11/1998 | Lee et al. |
| 5,851,991 | A | * | 12/1998 | Lee et al. ............ 514/12 |
| 5,910,487 | A |   | 6/1999  | Yew et al. |
| 5,912,239 | A |   | 6/1999  | Siegel et al. |
| 5,916,911 | A |   | 6/1999  | Shayman et al. |
| 5,925,628 | A |   | 7/1999  | Lee et al. |
| 5,935,936 | A |   | 8/1999  | Fasbender et al. |
| 5,939,401 | A |   | 8/1999  | Marshall et al. |
| 5,942,634 | A |   | 8/1999  | Siegel et al. |
| 5,945,442 | A |   | 8/1999  | Shayman et al. |
| 5,948,767 | A |   | 9/1999  | Scheule et al. |
| 5,948,925 | A |   | 9/1999  | Keynes et al. |
| 5,952,370 | A |   | 9/1999  | Shayman et al. |
| 5,968,502 | A |   | 10/1999 | Treco et al. |
| 6,030,995 | A |   | 2/2000  | Shayman et al. |
| 6,040,332 | A |   | 3/2000  | Shayman et al. |
| 6,051,598 | A |   | 4/2000  | Shayman et al. |
| 6,066,626 | A |   | 5/2000  | Yew et al. |
| 6,465,488 | B1 |  | 10/2002 | Butters et al. |
| 6,492,332 | B1 | * | 12/2002 | Demopulos et al. ............ 514/12 |
| 6,495,570 | B2 |  | 12/2002 | Jacob et al. |
| 6,610,703 | B1 |  | 8/2003  | Jacob et al. |
| 6,660,749 | B2 |  | 12/2003 | Butters et al. |
| 6,696,059 | B2 |  | 2/2004  | Jacob et al. |
| 7,312,324 | B2 |  | 12/2007 | Souza et al. |
| 2001/0044453 | A1 | | 11/2001 | Jacob et al. |
| 2002/0127213 | A1 | | 9/2002  | Jacob et al. |
| 2002/0142985 | A1 | | 10/2002 | Dwek et al. |
| 2003/0017139 | A1 | | 1/2003  | Souza et al. |
| 2005/0075305 | A1 | | 4/2005  | Dwek et al. |
| 2006/0074107 | A1 | | 4/2006  | Butters et al. |
| 2007/0178081 | A1 | | 8/2007  | Fan |

FOREIGN PATENT DOCUMENTS

| EP | 1 171 128 | 6/2003 |
| WO | WO 97/09441 | 3/1997 |
| WO | WO 98/11206 | 3/1998 |
| WO | WO 99/41399 | 8/1999 |
| WO | WO 99/41400 | 8/1999 |
| WO | WO 99/57296 | 11/1999 |
| WO | WO 00/09153 | 2/2000 |
| WO | WO 00/62779 | 10/2000 |
| WO | WO 00/62780 | 10/2000 |
| WO | WO 01/97829 | 12/2001 |

OTHER PUBLICATIONS

Kaye et al., 1990, Proc. Natl. Acad. Sci. USA, vol. 87, pp. 6922-6926.*
Skolnick et al., 2000, Trends in Biotech, vol. 18, p. 34-39.*
Abe et al., Feb. 2000, Kidney International, vol. 57, pp. 446-454.*
Bongiorno et al., 2003, JEADV, vol. 17, p. 676-679.*
Masson et al., 2004, Joint Bone Spine, vol. 71, p. 381-383.*
Wraith, J.E., 2006, J. of inherit. Metab. Dis., vol. 29, p. 442-447.*
Eto et al., 2004, J. Inherit. Metab. Dis., vol. 27, p. 411-415.*
Schiffmann et al., Jan. 2000, PNAS, vol. 97, No. 1, p. 365-370.*
Abe et al., Jun. 1, 2000, The Journal of Clinical Investigation, vol. 105, No. 11, p. 1563-1571.* Smallwood et al., 2002, Virology, vol. 304, p. 135-145.*
Chattopadhyay et al., 2004, Virus Research, vol. 99, p. 139-145.*
Andersson et al., "N-Butyldeoxygalactonojirimycin: A More Selective Inhibitor of Glycosphingolipid Biosynthesis than N-Butyldeoxynojirimycin, In Vitro and in Vivo," *Biochem. Pharmacol.* 59:821-829 (2000).
Barbon et al., "AAV8-Mediated Hepatic Expression of Acid Sphingomyelinase Corrects the Metabolic Defect in the Visceral Organs of a Mouse Model of Niemann-Pick Disease," *Mol. Ther.* 12(3):431-440 (2005).
Barton et al., "Replacement Therapy for Inherited Enzyme Deficiency—Macrophage-targeted Glucocerebrosidase for Gaucher's Disease," *N. Eng. J. Med.* 324(21):1464-1470 (1991).

(Continued)

*Primary Examiner* — Shin-Lin Chen
(74) *Attorney, Agent, or Firm* — Finnegan, Henderson, Farabow, Garrett & Dunner, LLP

(57) ABSTRACT

This invention provides various combinations of enzyme replacement therapy, gene therapy, and small molecule therapy for the treatment of lysosomal storage diseases.

3 Claims, 2 Drawing Sheets

OTHER PUBLICATIONS

Figure 1A:
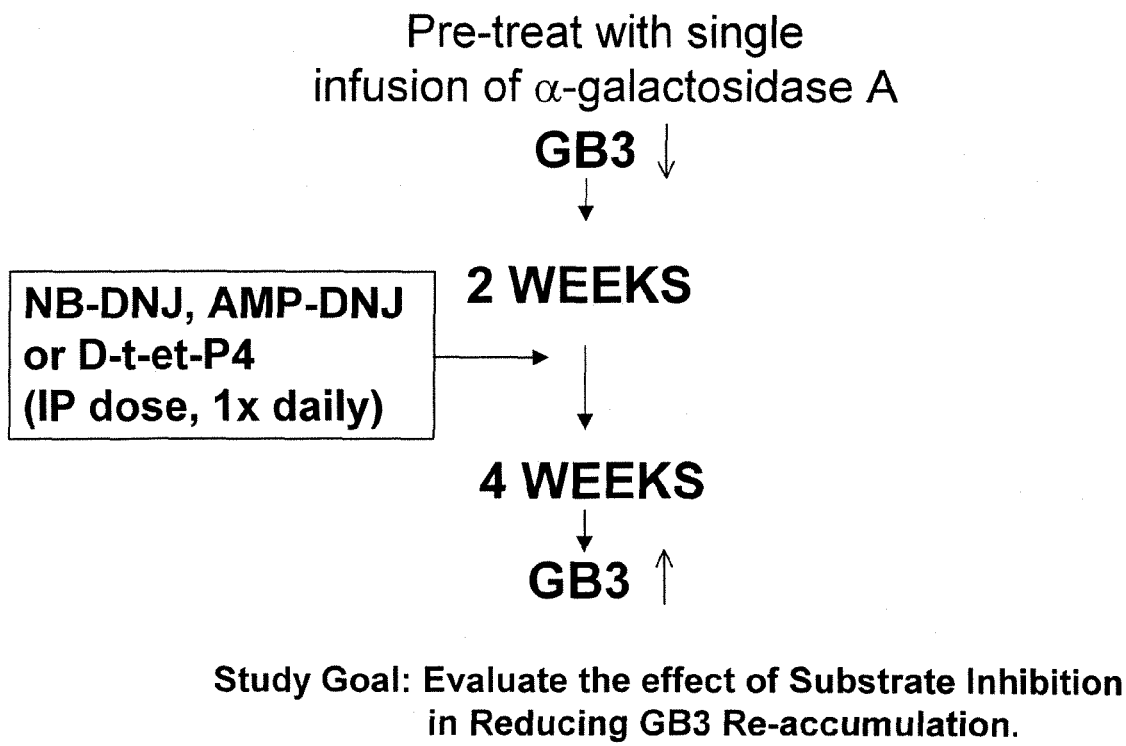

Beniaminovitz et al., "Prevention of Rejection in Cardiac Transplantation by Blockade of the Interleukin-2 Receptor with a Monoclonal Antibody," *N. Engl. J. Med.* 342(9):613-619 (2000).

Berard et al., "A Review of Interleukin-2 receptor Antagonists in Solid Organ Transplantation," *Pharmacotherapy* 19(10):1127-1137 (1999).

Beutler et al., "Gaucher disease: Four families with Previously UndeMcribed mutations," *Proc. Assoc. Am. Physicians* 108(3):179-184 (1996).

Bielicki et al., "Advantages of Using Same Species Enzyme for Replacement Therapy in a Feline Model of Mucopolysaccharidosis Type VI," *J. Biol. Chem.* 274(51):36335-36343 (1999).

Bodamer et al., "Dietary Treatment in Late-Onset Acid Maltase Deficiency," *Eur. J. Pediatr.* 156(Suppl. 1):S39-S42 (1997).

Bou-Gharios et al., "Lysomal Storage Diseases: Mechanisms of Enzyme Replacement Therapy," *Histochem. J.* 25(9):593-605 (1993).

Bowie et al., "Deciphering the Message in Protein Sequences: Tolerance to Amino Acid Substitutions," *Science* 247:1306-1310 (1990).

Brady et al., "Enzyme Replacement Therapy in Fabry Disease," *J. Inherit. Metab. Dis.*, 24(Suppl. 2):18-24 (2001).

Branco et al., "Selective Deletion of Antigen-Specific, Activated T Cells by a Humanized mAb to CD2 (MEDI-507) is Mediated by NK Cells," *Transplantation* 68(10):1588-1596 (1999).

Branden et al., *Introduction to Protein Structure.* 2d ed. Garland Publishing, Inc., New York: 1999; pp. 358-366.

Brooks, "Immune Response to Enzyme Rreplacement Therapy in Lysosomal Storage Disorder Patients and Animal Models," *Mol. Genet. Metabol.* 68:268-275 (1999).

Buechner et al., "Central Nervous System Involvement in Anderson-Fabry Disease: A Clinical and MRI Retrospective Study," *J. Neurol. Neurosurg. Psychiatry* 79(11):1249-1254 (2008) (published online Jun. 5, 2008).

Byers et al., "Effect of Enzyme Replacement Therapy on Bone Formation in a Feline Model of Mucopolysaccharidosis Type VI," *Bone* 21(5):425-431 (1997).

Cabrera-Salazar et al., "Adeno-Associated Viral-Mediated Gene Therapy of Lysosomal Storage Disorders" in *Lysosomal Storage Disorders.* Barranger and Cabrera-Salazar (Eds.) Springer Science+Business Media LLC: 2007; pp. 97-109.

Chen, "Glycogen Storage Diseases," *Harrison's Principles of Internal Medicine*, Fauci et al (Eds.), pp. 2176-2182 (McGraw-Hill, 14th ed., 1998).

Chirmule et al., "Readministration of Adenovirus Vector in Nonhuman Primate Lungs by Blockade of CD40-CD40 Ligand Interactions," *J. Virol.* 74(7):3345-3352 (2000).

Cleary et al., "The Presenting Features of Mucopolysaccharidosis Type IH (Hurler Syndrome)," *Acta. Paediatr.* 84:337-339 (1995).

Colville et al., "Early Presentation in the Mucopolysaccharide Disorders," *Child: Care, Health and Development* 22(1):31-36 (1996).

Cox et al., "Novel Oral Treatment of Gaucher Disease with N-butyldeoxynojirimycin (OGT 918) to Decrease Substrate Biosynthesis," *Lancet* 355:1481-1485 (2000).

Crawley et al., "Enzyme Replacement Therapy in a Feline Model of Maroteaux-Lamy Syndrome," *J. Clin. Invest.* 97(8):1864-1873 (1996).

Czartoryska et al., "Changes in Serum Chitotriosidase Activity with Cessation of Replacement Enzyme (Cerebrosidase) Administration in Gaucher Disease," *Clin. Biochem.* 33(2):147-149 (2000).

Czartoryska et al., "Serum Chitotriosidase Activity in Gaucher Patients on Enzyme Replacement Therapy (ERT)," *Clin. Biochem.* 31(5):417-420 (1998).

Daniele et al., "Uptake of Recombinant Iduronate-2-Sulfatase Into Neuronal and Glial Cells in Vitro," *Biochim. Biophys. Acta* 1588:203-209 (2002).

Den Tandt et al., "Marked Increase of Methylumbelliferyl-Tetra-N-Acetylchitotetraoside Hydrolase Activity in Plasma from Gaucher Disease Patients," *J. Inherit. Metab. Dis.* 19:344-350 (1996).

Desnick et al., "Enzyme Therapy in Fabry Disease: Differential in Vivo Plasma Clearance and Metabolic Effectiveness of Plasma and Splenic α-Galactosidase A Isozymes," *Proc. Natl. Acad. Sci. USA* 76(10):5326-5330 (1979).

Desnick et al., "Fabry Disease, an Under-Recognized Multisystemic Disorder: Expert Recommendations for Diagnosis, Management, and Enzyme Replacement Therapy," *Annals Int. Med.* 138:338-346 (2003).

Desnick et al., "α-Galactosidase A Deficiency: Fabry Disease," in *The Metabolic and Molecular Bases of Inherited Disease.* 7th ed. Scriver et al. (eds.) McGraw-Hill, New York: 1995; Ch. 89, pp. 2741-2784.

Dodelson De Kremer et al., "Actividad de la Chitotriosidasa Plasmatica en Pacientes Argentinos con Enfermedad de Gaucher, Diversas Lisosomopatias y en otras Metabolopatias Geneticas," *Medicina* (Buenos Aires) 57:677-684 (1997) (English Summary on p. 683).

Drucker et al., "Tay-Sachs Disease in an Israeli Arab Family: Tyr[26] → Stop in the α-Subunit of Hexosaminidase A," *Hum. Mutat.* 2:415-417 (1993).

Eckhoff et al., "The Safety and Efficacy of a Two-Dose Daclizumab (Zenapax) Induction Therapy in Liver Transplant Recipients," *Transplantation* 69(9):1867-1872 (2000).

Ekberg et al., "Daclizumab Prevents Acute Rejection and Improves Patient Survival Post Transplantation: 1 Year Pooled Analysis," *Transpl. Int.* 13:151-159 (2000).

Eng et al., "Safety and Efficacy of Recombinant Human α-Galactosidase a Replacement Therapy in Fabry's Disease," *N. Engl. J. Med.* 345(1):9-16 (2001).

Felice et al., "Clinical Variability in Adult-Onset Acid Maltase Deficiency: Report of Affected Sibs and Review of the Literature," *Medicine* 74(3):131-135 (1995).

Fellgiebel et al., "CNS Manifestations of Fabry's Disease," *Lancet Neurol.* 5:791-795 (2006).

Fishwild et al., "Differential Effects of Administration of a Human Anti-CD4 Monoclonal Antibody, HM6G, in Nonhuman Primates," *Clin. Immunol.* 92(2):138-152 (1999).

Gaziev et al., "Chronic Graft-Versus-Host Disease: Is There an Alternative to the Conventional Treatment?" *Bone Marrow Transplant.* 25:689-696 (2000).

Genzyme Corp., Prescribing Information for Fabrazyme® (Nov. 2006) (available online at http://www.fabrazyme.com/hcp/pi/fz_us_hc_pi.pdf).

Giugliani et al., "Management Guidelines for Mucopolysaccharidosis VI," *Pediatrics* 120(2):405-418 (2007).

Grabowski et al., "Enzyme Therapy in Type 1 Gaucher Disease: Comparative Efficacy of Mannose-terminated Glucocerebrosidase from Natural and Recombinant Sources," *Ann. Intern. Med.* 122:33-39 (1995).

Grady, "Cell Transplants Offer Hope for Severe Cases of Diabetes," *The New York Times*, Saturday, May 27, 2000, pp. A1 and A11.

Grewal, "Stroke in Fabry's Disease," *J. Neurol.* 241:153-156 (1994).

Guffon et al., "Follow-up of Nine Patients with Hurler Syndrome After Bone Marrow Transplantation," *J. Pediatr.* 133:119-125 (1998).

Gullingsrud et al., "Ocular Abnormalities in the Mucopolysaccharidoses After Bone Marrow Transplantation," *Ophthalmology* 105:1099-1105 (1998).

Gummert et al., "Newer Immunosuppressive Drugs: A review," *J. Am. Soc. Nephrol.* 10:1366-1380 (1999).

Guo et al., "Elevated Plasma Chitotriosidase Activity in Various Lysosomal Storage Disorders," *J. Inherit. Metab. Dis.* 18:717-722 (1995).

Hara et al., "Mutation Analysis of a Sandhoff Disease Patient in the Maronite Community in Cyprus," *Hum. Genet.* 94:136-140 (1994).

Henry, "Cyclosporine and Tacrolimus (FK506): a Comparison of Efficacy and Safety Profiles," *Clin. Transplant.* 13:209-220 (1999).

Hers, "Inborn Lysosomal Diseases", *Gastroenterology* 48(5):625-633 (1965).

Hirschhorn, "Glycogen Storage Disease Type II: Acid α-Glucosidase (Acid Maltase) Deficiency," in *The Metabolic and Molecular Bases of Inherited Disease.* 7th Edition. Scriver et al. (Eds.) McGraw-Hill, New York: 1995; Ch. 77, pp. 2443-2464.

Hollak et al., "Marked Elevation of Plasma Chitotriosidase Activity," *J. Clin. Invest.* 93:1288-1292 (1994).

Hong et al., "Immunosuppressive Agents in Organ Transplantation: Past, Present, and Future," *Semin. Nephrol.* 20(2):108-125 (2000).

Ideguchi et al., "Local-Adenovirus-Mediated CTLA-4-Immunoglobulin Expression Suppresses the Immune Responses to Adenovirus Vectors in the Brain," *Neuroscience* 95(1):217-226 (2000).

Ioannou et al., "Fabry Disease: Enzyme Replacement Therapy in α-Galactosidase A Deficient Mice," *Am. J. Hum. Genet.* 59(4):Suppl. A15, Abstr. 71 (1996).

Ioannou et al., "Fabry Disease: Preclinical Studies Demonstrate the Effectiveness of α-Galactosidase A Replacement in Enzyme-Deficient Mice," *Am. J. Hum. Genet.* 68:14-25 (2001).

Ito et al., "Induction of CTL Responses by Simultaneous Administration of Liposomal Peptide Vaccine with Anti-CD40 and Anti-CTLA-4 mAb," *J. Immunol.* 164:1230-1235 (2000).

Jeyakumar et al., "Delayed Symptom Onset and Increased Life Expectancy in Sandhoff Disease Mice Treated with N-Butyldeoxynojirimycin," *Proc. Natl. Acad. Sci. USA* 96:6388-6393 (1999).

Jeyakumar et al., "Enhanced Survival in Sandhoff Disease Mice Receiving a Combination of Substrate Deprivation Therapy and Bone Marrow Transplantation," *Blood* 97(1):327-329 (2001).

Kakavanos et al., "Immune Tolerance after Long-Term Enzyme-Replacement Therapy Among Patients who Have Mucopolysaccharidosis I," *Lancet* 361:1608-1613 (2003).

Kakkis et al., "Long-Term and High-Dose Trials of Enzyme Replacement Therapy in the Canine Model of Mucopolysaccharidosis I," *Biochem. Molec. Med.* 58:156-167 (1996).

Kakkis et al., "Overexpression of the Human Lysosomal Enzyme α-L-iduronidase in Chinese hamster Ovary Cells," *Prot. Express. Purif.* 5:225-232 (1994).

Kakkis et al., "Successful Induction of Immune Tolerance to Enzyme Replacement Therapy in Canine Mucopolysaccharidosis I," *Proc. NatL Acad. Sci. USA* 101(3):829-834 (2004).

Keeling et al., "Gentamicin-Mediated Suppression of Hurler Syndrome Stop Mutations Restores a Low Level of α-L-iduronidase Activity and Reduces Lysosomal Glycosaminoglycan Accumulation," *Hum. Molec. Genet.* 10(3):291-299 (2001).

Kikuchi et al., "Clinical and Metabolic Correction of Pompe Disease by Enzyme Therapy in Acid Maltase-Deficient Quail," *J. Clin. Invest.* 101(4):827-833 (1998).

Ko et al., "Atypical Fabry's Disease—An Oligosymptomatic Variant," *Arch. Pathol. Lab. Med.* 120:86-89 (1996).

Kolodny et al., "Storage Diseases of the Reticuloendothelial System," in Nathan and Oski's *Hematology of Infancy and Childhood*. 5th Edition. vol. 2. David G. Nathan and Stuart H. Orkin (Eds.) W.B. Saunders Co.: 1998; Ch. 38, pp. 1461-1507.

Kurlberg et al., "Blockade of the B7-CD28 Pathway by CTLA4-Ig Counteracts Rejection and Prolongs Survival in Small Bowel Transplantation," *Scand. J. Immunol.* 51:224-230 (2000).

Lee et al., "Improved Inhibitors of Glucosylceramide Synthase," *J. Biol. Chem.* 274:14662-14669 (1999).

Leonard et al., "Cytokine Receptor Signaling Pathways," *J. Allergy Clin. Immunol.* 105:877-888 (2000).

Marinova-Mutafchieva et al., "A Comparative Study Into the Mechanisms of Action of Anti-Tumor Necrosis Factor α, Anti-CD4, and Combined Anti-Tumor Necrosis Factor α/anti-CD4 Treatment in Early Collagen-Induced Arthritis," *Arthritis Rheum.* 43(3):638-644 (2000).

Masterson et al., "Hip Dysplasia in Hurler's Syndrome: Orthopaedic Management After Bone Marrow Transplantation," *J. Pediatr. Ortho.* 16:731-733 (1996).

McEachern et al., "AAV8-Mediated Expression of Glucocerebrosidase Ameliorates the Storage Pathology in the Visceral Organs of a Mouse Model of Gaucher Disease," *J. Gene Med.* 8:719-729 (2006).

McGovern, "Lysosomal Storage Diseases," *Harrison's Principles of Internal Medicine*, Fauci et al (Eds.), pp. 2169-2176 (McGraw-Hill, 14th ed., 1998).

Mehta et al. Eds., *Fabry disease Perspectives from 5 years of FOS*, Table of Contents pp. vii-x (Oxford PharmaGenesis™ Ltd., 2006).

Mendez et al., "The Vascular Dementia of Fabry's Disease," *Dement. Geriatr. Cogn. Disord.* 8:252-257 (1997).

Miller et al., "Genetic Studies of the *lac* Repressor," *J. Mol. Biol.* 131:191-222 (1979).

Mistry et al., "A Practical Approach to Diagnosis and Management of Gaucher's Disease," *Baillière's Clin. Haematol.* 10:817-838 (1997).

Moder, "New Medications for Use in Patients with Rheumotoid Arthritis," *Ann. Allergy Asthma Immunol.* 84:280-287 (2000).

Moore et al., "The Cerebral Vasculopathy of Fabry Disease," *J. Neurol. Sci.* 257:258-263 (2007).

Morales, "Gaucher's Disease: A Review," *Ann. Pharmacother.* 30:381-388 (1996).

Nakao, "An Atypical Variant of Fabry's Disease in Men with Left Ventricular Hypertrophy," *N. Engl. J. Med.* 333:288-293 (1995).

Neufeld et al., The Mucopolysaccharidoses,: in *The Metabolic and Molecular Bases of Inherited Diseases*. 7th Edition. Scriver et al. (Eds.) McGraw-Hill, New York: 1995; Ch. 78, pp. 2465-2494.

Neufeld, "Lysosomal Storage Diseases," *Annu. Rev. Biochem.* 60:257-280 (1991).

Nevins, "Overview of New Immunosuppressive Therapies," *Curr. Opin. Pediatr.* 12:146-150 (2000).

O'Connor et al., "Enzyme Replacement Therapy for Murine Mucopolysaccharidosis Type VII Leads to Improvements in Behavior and Auditory Function" *J. Clin. Invest.* 101(7):1394-1400 (1998).

Oberholzer et al., "Cytokine Signaling-Regulation of the Immune Response in Normal and Critically Ill States," *Crit. Care Med.* 28(4 Suppl.):N3-N12 (2000).

Ohshima et al., "α-Galactosidase A deficient mice: A model of Fabry disease," *Proc. Natl. Acad. Sci. USA* 94:2540-2544 (1997).

Okumiya et al., "Two Novel Mutations in the α-Galactosidase Gene in Japanese Classical Hemizygotes with Fabry Disease," *Jpn. J. Human Genet.* 41:313-321 (1996).

Oshima et al., "Cloning, Sequencing, and Expression of cDNA for Human β-Glucuronidase," *Proc. Natl. Acad. Sci. USA* 84:685-689 (1987).

Overkleeft et al., "Generation of Specific Deoxynojirimycin-Type Inhibitors of the Non-Lysosomal Glucosylceramidase," *J. Biol. Chem* 273(41):26522-26527 (1998).

Paladin Labs Inc., "Conditional Approval of Replagal™ (agalsidase alfa): Fact Sheet" Paladin Labs Inc., Feb. 6, 2004 (Health Canada). Available online at http://www.hc-sc.gc.ca/dhp-mps/prodpharma/notices-avis/conditions/replagal_fs_fd_068304-eng.php.

Pastores et al., "Current and Emerging Therapies for the lysosomal Storage Disorders," *Expert Opin. Emerging Drugs* 10(4):891-902 (2005).

Pastores et al., "Enzyme Therapy in Gaucher Disease Type 1: Dosage Efficacy and Adverse Effects in 33 Patients Treated for 6 to 24 Months," *Blood* 82(2):408-416 (1993).

Peltola et al., "Characterization of a Point Mutation in Aspartylglucosaminidase Gene: Evidence for a Readthrough of a Translational Stop Codon," *Hum. Molec. Genet.* 3(12):2237-2242 (1994).

Peters et al., "Hurler Syndrome: II. Outcome of HLA-Genotypically Identical Sibling and HLA-Haploidentical Related Donor Bone Marrow Transplantation in Fifty-Four Children," *Blood* 91(7):2601-2608 (1998).

Peters et al., "Hurler Syndrome: Past, Present and Future," *J. Pediatr.* 133(1):7-9 (1998).

Platt et al., "Prevention of Lysosomal Storage in Tay-Sachs Mice Treated with N-Butyldeoxynojirimycin," *Science* 276:428-431 (1997).

Ponce et al., "Enzyme Therapy in Gaucher Disease Type 1: Effect of Neutralizing Antibodies to Acid β-Glucosidase," *Blood* 90:43-48 (1997).

Ponticelli et al., "Promising New Agents in the Prevention of Transplant Rejection," *Drugs R&D* 1:55-60 (1999).

Potter et al., "Review-The Use of Immunosuppressive Agents to Prevent Neutralizing Antibodies Against a Transgene Product," *Ann. N. Y. Acad. Sci.* 875:159-174 (1999).

Przepiorka et al., "A Phase II Study of BTI-322, a Monoclonal Anti-CD2 Antibody, for Treatment of Steriod-Resistant Acute Graft-Versus-Host Disease," *Blood* 92(11):4066-4071 (1998).

Qi et al., "Effect of Tacrolimus (FK506) and Sirolimus (Rapamycin) Mono- and Combination Therapy in Prolongation of Renal Allograft Survival in the Monkey," *Transplantation* 69:1275-1283 (2000).

Reuser et al., "Glycogenosis Type II (Acid Maltase Deficiency)," *Muscle & Nerve* Suppl. 3:S61-S69 (1995).

Rosenthal et al., "Enzyme Replacement Therapy for Gaucher Disease: Skeletal Responses to Macrophage-targeted Glucocerebrosidase," *Pediatrics* 96(4):629-637 (1995).

Rubinstein et al., "Recent Advances in Cytokines, Cytokine Receptors and Signal Transduction," *Cytokine & Growth Factor Rev.* 9(2):175-181 (1998).

Ryan et al., "Clinical outcomes and Insulin Secretion after Islet Transplantation with the Edmonton Protocol," *Diabetes* 50:710-719 (2001).

Sakuraba et al., "Identification of Point Mutations in the α-Galactosidase A Gene in Classical and Atypical Hemizygotes with Fabry Disease," *Am. J. Hum. Genet.* 47:784-789 (1990).

Sands et al., "Murine Mucopolysaccharidosis Type VII: Long Term Therapeutic Effects of Enzyme Replacement and Enzyme Replacement Followed by Bone Marrow Transplantation," *J. Clin. Invest.* 99(7):1596-1605 (1997).

Scaravilli et al., "Enzyme Replacement in Grafted Nerve of *Twitcher* Mouse," *Nature* 305(5936):713-715 (Oct. 20, 1983).

Schiffmann et al., "Enzyme Replacement Therapy in Fabry Disease: a Randomized Controlled Trial," *JAMA* 285(21):2743-2749 (2001).

Shapiro et al., "Islet Transplantation in Seven Patients With Type 1 Diabetes Mellitus Using a Glucocorticoid Free Immunosuppressive Regimen," *N. Engl. J. Med.* 343(4):230-238 (2000).

Shayman et al., "Inhibitors of Glucosylceramide Synthase," *Meth. Enzymol.* 311:373-387 (1999).

Shelley et al., "Painful Fingers, Heat Intolerance, and Telangiectases of the Ear: Easily Ignored Childhood Signs of Fabry Disease," *Pediatric Dermatol.* 12(3):215-219 (1995).

Shull et al., "Enzyme Replacement in a Canine Model of Hurler Syndrome," *Proc. Natl. Acad. Sci. USA* 91:12937-12941 (1994).

Slavik et al., "CD28/CTLA-4 and CD80/CD86 Families," *Immunol. Res.* 19(1):1-24 (1999).

Sukegawa-Hayasaka et al., "Effect of Hunter Disease (Mucopolysaccharidosis Type II) Mutations on Molecular Phenotypes of Iduronate-2-Sulfatase: Enzymatic Activity, Protein Processing and Structural Analysis," *J. Inherit. Metab. Dis.* 29(6):755-761 (2006).

Takahashi et al., "Identification and Expression of Five Mutations in the Human Acid Sphingomyelinase Gene Causing Types A and B Niemann-Pick Disease," *J. Biol. Chem.* 267(18):12552-12558 (1992).

Tanaka et al., "Novel Mutations, Including the Second Most Common in Japan, in the β-Hexosaminidase α Subunit Gene, and a Simple Screening of Japanese Patients with Tay-Sachs Disease," *J. Hum. Genet.* 44:91-95 (1999).

Tsuji et al., "Signal Sequence and DNA-Mediated Expression of Human Lysosomal α-Galactosidase A," *Eur. J. Biochem.* 165:275-280 (1987).

U.S. Food and Drug Administration, Department of Health and Human Services Approval Letter to Genzyme Corporation regarding U.S. License No. 1596, dated Apr. 24, 2003 (available online at http://www.fda.gov/cder/foi/appletter/2003/agalgen042403L.htm).

Van Der Ploeg et al., "Breakdown of Lysosomal Glycogen in Cultured Fibroblasts from Glycogenosis Type II Patients After Uptake of Acid α-Glucosidase," *J. Neurolog. Sci.* 79:327-336 (1987).

Van Der Ploeg et al., "Intravenous Administration of Phosphorylated Acid α-Glucosidase Leads to Uptake of Enzyme in Heart and Skeletal Muscle of mice," *J. Clin. Invest.* 87:513-518 (1991).

Van Der Ploeg et al., "Prospect for Enzyme Therapy in Glycogenosis II Variants: A Study on Cultured Muscle Cells," *J. Neurol.* 235:392-396 (1988).

Van Der Ploeg et al., "Receptor-Mediated Uptake of Acid α-Glucosidase Corrects Lysosomal Glycogen Storage in Cultured Skeletal Muscle," *Pediatr. Res.* 24(1):90-94 (1988).

Van Heest et al., "Surgical Treatment of Carpal Tunnel Syndrome and Trigger Digits in Children with Mucopolysaccharide Storage Disorders," *J. Hand Surgery* 23A:236-243 (1998).

Van Hove et al., "High-Level Production of Recombinant Human Lysosomal Acid α-Glucosidase in Chinese Hamster Ovary Cells which Targets to Heart Muscle and Corrects Glycogen Accumulation in Fibroblasts from Patients with Pompe Disease," *Proc. Natl. Acad. Sci. USA* 93:65-70 (1996).

Vogler et al., "Enzyme Replacement in Murine Mucopolysaccharidosis Type VII: Neuronal and Glial response to β-Glucuronidase Requires Early Initiation of Enzyme Replacement Therapy," *Pediatr. Res.* 45(6):838-844 (1999).

Voskoboeva et al., "Four Novel Mutant Alleles of the Arylsulfatase B Gene in Two Patients with Intermediate Form of Mucopolysaccharidosis VI (Maroteaux-Lamy syndrome)," *Hum. Genet.* 93:259-264 (1994).

Wilcox et al., "Long-Term Safety and Efficacy of Enzyme Replacement Therapy for Fabry Disease," *Am. J. Hum. Genet.* 75:65-74 (2004).

Wiseman et al., "Daclizumab: A Review of its Use in the Prevention of Acute Rejection in Renal Transplant Recipients," *Drugs* 58(6):1029-1042 (1999).

Wraith, "Advances in the Treatment of Lysosomal Storage Disease" *Dev. Med. Child Neurol.* 43:639-646 (2001).

Yang et al., "Pedigree Analysis of α-L-Fucosidase Gene Mutations in Fucosidosis Family," *Biochim. Biophys. Acta* 1182:245-249 (1993).

Yew et al. "CpG-Depleted Plasmid DNA Vectors with Enhanced Safety and Long-Term Gene Expression in Vivo," *Mol. Ther.* 5(6):731-738 (2002).

Young et al., "Plasma Chitotriosidase Activity in Gaucher Disease Patients Who Have Been Treated Either by Bone Marrow Transplantation or by Enzyme Replacement Therapy with Alglucerase," *J. Inherit. Metab. Dis.* 20:595-602 (1997).

Zarate et al., "Lysosomal Storage Disease 3: Fabry's disease," *Lancet* 372:1427-1435 (2008).

Zhang et al., "Impact of Premature Stop Codons on mRNA Levels in Infantile Sandhoff Disease," *Hum. Molec. Genet.* 3(1):139-145 (1994).

Ziegler et al., "AAV2 Vector Harboring a Liver-Restricted Promoter Facilitates Sustained Expression of Therapeutic Levels of α-Galactosidase A and the Induction of Immune Tolerance in Fabry Mice," *Mol. Ther.* 9(2):231-240 (2004).

Ziegler et al., "Correction of Enzymatic and Lysosomal Storage Defects in Fabry Mice by Adenovirus-Mediated Gene Transfer," *Hum. Gene Ther.* 10(10):1667-1682 (1999).

Ziegler et al., "Correction of the Nonlinear Dose Response Improves the Viability of Adenoviral Vectors for Gene Therapy of Fabry Disease," *Hum. Gene Ther.* 13:935-945 (2002).

Office Action issued in parent U.S. Appl. No. 09/884,526, mailed May 29, 2003.

Office Action issued in parent U.S. Appl. No. 09/884,526, mailed Feb. 18, 2004.

Office Action issued in parent U.S. Appl. No. 09/884,526, mailed Aug. 25, 2004.

Office Action issued in parent U.S. Appl. No. 09/884,526, mailed Jan. 31, 2005.

Office Action issued in parent U.S. Appl. No. 09/884,526, mailed Aug. 10, 2005.

Office Action issued in parent U.S. Appl. No. 09/884,526, mailed Mar. 6, 2006.

Office Action issued in parent U.S. Appl. No. 09/884,526, mailed Oct. 17, 2006.

Office Action issued in U.S. Appl. No. 10/758,773, mailed Feb. 12, 2008.

Office Action issued in U.S. Appl. No. 10/758,773, mailed Jun. 1, 2007.

Office Action issued in U.S. Appl. No. 10/758,773, mailed Sep. 26, 2008.

* cited by examiner

COMBINATION ENZYME REPLACEMENT AND SMALL MOLECULE THERAPY FOR TREATMENT OF LYSOSOMAL STORAGE DISEASES

This is a continuation divisional of application Ser. No. 09/884,526, filed Jun. 19, 2001, which claims the benefit of U.S. Provisional Application No. 60/212,377, filed Jun. 19, 2000, both of which are incorporated herein by reference.

1. FIELD OF THE INVENTION

The present invention relates generally to the field of therapeutics for lysosomal storage diseases. More specifically, the invention relates to various combinations of enzyme replacement therapy, gene therapy, and small molecule therapy for the treatment of lysosomal storage diseases.

2. BACKGROUND OF THE INVENTION

Each of the over thirty known lysosomal storage diseases (LSDs) is characterized by a similar pathogenesis, namely, a compromised lysosomal hydrolase. Generally, the activity of a single lysosomal hydrolytic enzyme is reduced or lacking altogether, usually due to inheritance of an autosomal recessive mutation. As a consequence, the substrate of the compromised enzyme accumulates undigested in lysosomes, producing severe disruption of cellular architecture and various disease manifestations.

2.1 Lysosomal Storage Diseases

Gaucher's disease, first described by Phillipe C. E. Gaucher in 1882, is the oldest and most common lysosomal storage disease known. Type I is the most common among three recognized clinical types and follows a chronic course which does not involve the nervous system. Types 2 and 3 both have a CNS component, the former being an acute infantile form with death by age two and the latter a subacute juvenile form. The incidence of Type 1 Gaucher's disease is about one in 50,000 live births generally and about one in 400 live births among Ashkenazim (see generally Kolodny et al., 1998, "Storage Diseases of the Reticuloendothelial System", In: Nathan and Oski's Hematology of Infancy and Childhood, 5th ed., vol. 2, David G. Nathan and Stuart H. Orkin, Eds., W.B. Saunders Co., pages 1461-1507). Also known as glucosylceramide lipidosis, Gaucher's disease is caused by inactivation of the enzyme glucocerebrosidase and accumulation of glucocerebroside. Glucocerebrosidase normally catalyzes the hydrolysis of glucocerebroside to glucose and ceramide. In Gaucher's disease, glucocerebroside accumulates in tissue macrophages which become engorged and are typically found in liver, spleen and bone marrow and occasionally in lung, kidney and intestine. Secondary hematologic sequelae include severe anemia and thrombocytopenia in addition to the characteristic progressive hepatosplenomegaly and skeletal complications, including osteonecrosis and osteopenia with secondary pathological fractures.

Fabry disease is an X-linked recessive LSD characterized by a deficiency of α-galactosidase A (α-Gal A), also known as ceramide trihexosidase, which leads to vascular and other disease manifestations via accumulation of glycosphingolipids with terminal α-galactosyl residues, such as globotriaosylceramide (GL-3) (see generally Desnick R J et al., 1995, α-Galactosidase A Deficiency: Fabry Disease, In: The Metabolic and Molecular Bases of Inherited Disease, Scriver et al., eds., McGraw-Hill, New York, 7$^{th}$ ed., pages 2741-2784). Symptoms may include anhidrosis (absence of sweating), painful fingers, left ventricular hypertrophy, renal manifestations, and ischemic strokes. The severity of symptoms varies dramatically (Grewal R P, 1994, Stroke in Fabry's Disease, J. Neurol. 241, 153-156). A variant with manifestations limited to the heart is recognized, and its incidence may be more prevalent than once believed (Nakao S, 1995, An Atypical Variant of Fabry's Disease in Men with Left Ventricular Hypertrophy, N. Engl. J. Med. 333, 288-293). Recognition of unusual variants can be delayed until quite late in life, although diagnosis in childhood is possible with clinical vigilance (Ko Y H et al., 1996, Atypical Fabry's Disease—An Oligosymptomatic Variant, Arch. Pathol. Lab. Med. 120, 86-89; Mendez M F et al., 1997, The Vascular Dementia of Fabry's Disease, Dement. Geriatr. Cogn. Disord. 8, 252-257; Shelley E D et al., 1995, Painful Fingers, Heat Intolerance, and Telangiectases of the Ear: Easily Ignored Childhood Signs of Fabry Disease, Pediatric Derm. 12, 215-219). The mean age of diagnosis of Fabry disease is 29 years.

Niemann-Pick disease, also known as sphingomyelin lipidosis, comprises a group of disorders characterized by foam cell infiltration of the reticuloendothelial system. Foam cells in Niemann-Pick become engorged with sphingomyelin and, to a lesser extent, other membrane lipids including cholesterol. Niemann-Pick is caused by inactivation of the enzyme sphingomyelinase in Types A and B disease, with 27-fold more residual enzyme activity in Type B (see Kolodny et al., 1998, Id.). The pathophysiology of major organ systems in Niemann-Pick can be briefly summarized as follows. The spleen is the most extensively involved organ of Type A and B patients. The lungs are involved to a variable extent, and lung pathology in Type B patients is the major cause of mortality due to chronic bronchopneumonia. Liver involvement is variable, but severely affected patients may have life-threatening cirrhosis, portal hypertension, and ascites. The involvement of the lymph nodes is variable depending on the severity of disease. Central nervous system (CNS) involvement differentiates the major types of Niemann-Pick. While most Type B patients do not experience CNS involvement, it is characteristic in Type A patients. The kidneys are only moderately involved in Niemann Pick disease.

The mucopolysaccharidoses (MPS) comprise a group of LSDs caused by deficiency of enzymes which catalyze the degradation of specific glycosaminoglycans (mucopolysaccharides or GAGs) known as dermatan sulfate and heparan sulfate. GAGs contain long unbranched polysaccharides characterized by a repeating disaccharide unit and are found in the body linked to core proteins to form proteoglycans. Proteoglycans are located primarily in the extracellular matrix and on the surface of cells where they lubricate joints and contribute to structural integrity (see generally Neufeld et al., 1995, The Mucopolysaccharidoses, In: The Metabolic and Molecular Bases of Inherited Diseases, Scriver et al., eds., McGraw-Hill, New York, 7$^{th}$ ed., pages 2465-2494).

The several mucopolysaccharidoses are distinguished by the particular enzyme affected in GAG degradation. For example, MPS I (Hurler-Scheie) is caused by a deficiency of α-L-iduronidase which hydrolyzes the terminal α-L-iduronic acid residues of dermatan sulfate. Symptoms in MPS I vary along a clinical continuum from mild (MPS IS or Scheie disease) to intermediate (MPS IHS or Hurler-Scheie disease) to severe (MPS IH or Hurler disease), and the clinical presentation correlates with the degree of residual enzyme activity. The mean age at diagnosis for Hurler syndrome is about nine months, and the first presenting symptoms are often among the following: coarse facial features, skeletal abnormalities, clumsiness, stiffness, infections and hernias (Cleary M A and Wraith J E, 1995, The Presenting Features of Mucopolysaccharidosis Type IH (Hurler Syndrome), Acta. Paediatr. 84, 337-339; Colville G A and Bax M A, 1996, Early Presentation in the Mucopolysaccharide Disorders, Child: Care, Health and Development 22, 31-36).

Other examples of mucopolysaccharidoses include Hunter (MPS II or iduronate sulfatase deficiency), Morquio (MPS IV; deficiency of galactosamine-6-sulfatase and β-galactosidase in types A and B, respectively) and Maroteaux-Lamy (MPS VI or arylsulfatase B deficiency) (see Neufeld et al., 1995, Id.; Kolodny et al., 1998, Id.).

Pompe disease (also known as glycogen storage disease type II, acid maltase deficiency and glycogenosis type II) is an autosomal recessive LSD characterized by a deficiency of α-glucosidase (also known as acid α-glucosidase and acid maltase). The enzyme α-glucosidase normally participates in the degradation of glycogen to glucose in lysosomes; it can also degrade maltose (see generally Hirschhorn R, 1995, Glycogen Storage Disease Type II: Acid α-Glucosidase (Acid Maltase) Deficiency, In: The Metabolic and Molecular Bases of Inherited Disease, Scriver et al., eds., McGraw-Hill, New York, $7^{th}$ ed., pages 2443-2464). The three recognized clinical forms of Pompe disease (infantile, juvenile and adult) are correlated with the level of residual α-glucosidase activity (Reuser A J et al., 1995, Glycogenosis Type II (Acid Maltase Deficiency), Muscle & Nerve Supplement 3, S61-S69).

Infantile Pompe disease (type I or A) is most common and most severe, characterized by failure to thrive, generalized hypotonia, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually die before reaching 20 years of age due to respiratory failure. Adult Pompe disease (type III or C) often presents as a slowly progressive myopathy in the teenage years or as late as the sixth decade (Felice K J et al., 1995, Clinical Variability in Adult-Onset Acid Maltase Deficiency: Report of Affected Sibs and Review of the Literature, Medicine 74, 131-135).

In Pompe, it has been shown that α-glucosidase is extensively modified post-translationally by glycosylation, phosphorylation, and proteolytic processing. Conversion of the 110 kilodalton (kDa) precursor to 76 and 70 kDa mature forms by proteolysis in the lysosome is required for optimum glycogen catalysis.

2.2 Therapies for Lysosomal Storage Diseases

Several approaches are being used or pursued for the treatment of LSDs, most of which focus on gene therapy or enzyme replacement therapy for use alone in disease management. Additionally, researchers have identified a number of small molecules for use alone in the management of LSDs. Other, disease-specific approaches, are also under consideration.

Gene Therapy

Replacement of the defective enzyme in a patient with Fabry Disease is considered feasible using a recombinant retrovirus carrying the cDNA encoding α-Gal A to transfect skin fibroblasts obtained from Fabry patients (Medin J A et al., 1996, Correction in Trans for Fabry Disease: Expression, Secretion, and Uptake of α-Galactosidase A in Patient-Derived Cells Driven by a High-Titer Recombinant Retroviral Vector, Proc. Natl. Acad. Sci. USA 93, 7917-7922).

In vitro studies have also suggested that gene therapy may be feasible in Pompe disease. Vectors are being developed from both recombinant retrovirus and recombinant adenovirus (Zaretsky JZ et al., 1997, Retroviral Transfer of Acid α-Glucosidase cDNA to Enzyme-Deficient Myoblasts Results in Phenotypic Spread of the Genotypic Correction by Both Secretion and Fusion, Human Gene Therapy 8, 1555-1563; Pauly D F et al., 1998, Complete Correction of Acid α-Glucosidase Deficiency in Pompe Disease Fibroblasts in Vitro, and Lysosomally Targeted Expression in Neonatal Rat Cardiac and Skeletal Muscle, Gene Therapy 5, 473-480).

Additionally, transfer and expression of the normal α-L-iduronidase gene into autologous bone marrow by retroviral gene transfer has also been demonstrated in non-clinical studies of Hurler Syndrome (Fairbaim et al., 1996, Long-Term in vitro Correction of α-L-Iduronidase Deficiency (Hurler Syndrome) in Human Bone Marrow, Proc. Natl. Acad. Sci. U.S.A. 93, 2025-2030).

Enzyme Replacement Therapy

Enzyme replacement therapy involves administration, preferably intravenous, of an exogenously-produced natural or recombinant enzyme. Enzyme replacement therapy proof-of-principle has been established in a Hurler animal model (Shull R M et al., 1994, Enzyme Replacement in a Canine Model of Hurler Syndrome, Proc. Natl. Acad. Sci. USA 91, 12937-12941). Others have developed effective methods for cell culture expression of recombinant enzyme in sufficient quantities to be collected for therapeutic use (Kakkis E D et al., 1994, Overexpression of the Human Lysosomal Enzyme α-L-Iduronidase in Chinese Hamster Ovary Cells, Prot. Express. Purif. 5, 225-232). However, one unsolved problem is the development of antibodies against the replacement enzyme after long term therapy (Kakkis E D et al., 1996, Long-Term and High-Dose Trials of Enzyme Replacement Therapy in the Canine Model of Mucopolysaccharidosis I, Biochem. Molec. Med. 58, 156-167).

The use of enzyme replacement therapy has also been investigated for patients with Pompe disease. However, effective enzyme replacement therapy requires the use of a precursor α-glucosidase molecule for correct targeting to lysosomes (Van Der Ploeg A T et al., 1987, Breakdown of Lysosomal Glycogen in Cultured Fibroblasts from Glycogenosis Type II Patients After Uptake of Acid α-Glucosidase, J. Neurolog. Sci. 79, 327-336; Van Der Ploeg, A T et al., 1991, Intravenous Administration of Phosphorylated Acid α-Glucosidase Leads to Uptake of Enzyme in Heart and Skeletal Muscle of Mice, J. Clin. Invest. 87, 513-518; Van Der Ploeg A T et al., 1988, Prospect for Enzyme Replacement Therapy in Glycogenosis II Variants: A study on Cultured Muscle Cells, J. Neurol. 235, 392-396; Van Der Ploeg A T et al., 1988, Receptor-Mediated Uptake of Acid α-Glucosidase Corrects Lysosomal Glycogen Storage in Cultured Skeletal Muscle, Pediatr. Res. 24, 90-94). Despite the requirement for a robust production method for human recombinant α-glucosidase, animal and in vitro studies have provided reason for optimism (Van Hove J L K et al., 1996, High-Level Production of Recombination Human Lysosomal Acid α-Glucosidase in Chinese Hamster Ovary Cells Which Targets to Heart Muscle and Corrects Glycogen Accumulation in Fibroblasts from Patients with Pompe Disease, Proc. Natl. Acad. Sci. USA 93, 65-70; Kikuchi T et al., 1998, Clinical and Metabolic Correction of Pompe Disease by Enzyme Therapy in Acid Maltase-Deficient Quail, J. Clin. Invest. 101, 827-833).

Small Molecule Therapy

Recently, a variety of studies have been conducted using several small molecules for storage disease therapy. One class of molecules inhibits upstream generation of lysosomal hydrolase substrate to relieve the input burden to the defective enzyme. This approach has been dubbed "substrate deprivation" therapy. One example of this class of molecules is N-butyldeoxynojirimycin (NB-DNJ), an inhibitor of the ceramide-specific glucosyltransferase (i.e. glucosylceramide synthase) which catalyzes the first step in the synthesis of glycosphingolipids (GSLs). NB-DNJ has been tested in mouse models of Sandhoff disease (Jeyakumar et al., 1999, Proc. Natl. Acad. Sci. USA 96, 6388-6393), Tay-Sachs disease (Platt et al., 1997, Science 276, 428-431), as well as in humans with Gaucher's disease (Cox et al., 2000, Lancet 355, 1481-1485), resulting in an amelioration of symptoms in each of these diseases. A variety of deoxynojirimycin (DNJ) derivatives have also been synthesized as research tools intended for the selective inhibition of the non-lysosomal glucosylceramidase at concentrations in which glucosylceramide synthase and other enzymes are not affected (Overkleeft et al., 1998, J. Biol. Chem. 273, 26522-26527). Certain uses of glucosylceramide synthase inhibitors of the DNJ type either alone (WO 00/62780) or in combination with a glycolipid degrading enzyme (WO 00/62779) have been described.

Another example of the substrate deprivation class of molecules are the amino ceramide-like small molecules which have been developed for glucosylceramide synthase inhibition. Glucosylceramide synthase catalyzes the first glycosylation step in the synthesis of glucosylceramide-based glycosphingolipids. Glucosylceramide itself is the precursor of hundreds of different glycosphingolipids. Amino ceramide-like compounds have been developed for use in Fabry disease (Abe et al., 2000, J. Clin. Invest. 105, 1563-1571; Abe et al., 2000, Kidney Int'l 57, 446-454) and Gaucher's disease (Shayman et al., 2000, Meth. Enzymol. 31, 373-387; U.S. Pat. Nos. 5,916,911; 5,945,442; 5,952,370; 6,030,995; 6,040,332 and 6,051,598). A variety of amino ceramide-like analogues have been synthesized as improved inhibitors of glucosylceramide synthase (see e.g. Lee et al., 1999, J. Biol. Chem. 274, 14662-14669).

Aminoglycosides such as gentamicin and G418 are small molecules which promote read-through of premature stop-codon mutations. These so-called stop-mutation suppressors have been used in Hurler cells to restore a low level of α-L-iduronidase activity (Keeling et al., 2001, Hum. Molec. Genet. 10, 291-299). They have also been developed for use in treating cystic fibrosis individuals having stop mutations (U.S. Pat. No. 5,840,702).

Other Therapies

Various other, disease-specific, treatments have been attempted. For example, a high protein diet in adult Pompe has been suggested to combat muscle wasting, but was effective in improving respiratory or muscle function in only 25% of individuals (Bodamer O A F et al., 1997, Dietary Treatment in Late-Onset Acid Maltase Deficiency, Eur. J. Pediatr. 156, S39-S42). In Hurler disease, bone marrow transplantation has shown limited benefits but carries significant risks (Guffon N et al., 1998, Follow-up of Nine Patients with Hurler Syndrome After Bone Marrow Transplantation, J. Pediatr. 133, 119-125; Gullingsrud E O et al., 1998, Ocular Abnormalities in the Mucopolysaccharidoses After Bone Marrow Transplantation, Ophthalmology 105, 1099-1105; Masterson E L et al., 1996, Hip Dysplasia in Hurler's Syndrome: Orthopaedic Management After Bone Marrow Transplantation, J. Pediatric Orthopaedics 16, 731-733; Peters C et al., 1998, Hurler Syndrome: Past, Present and Future, J. Pediatr. 133, 7-9; Peters C et al., 1998, Hurler Syndrome: II. Outcome of HLA-Genotypically Identical Sibling and HLA-Haploidentical: Related Donor Bone Marrow Transplantation in Fifty-Four Children, Blood 91, 2601-2608). Early surgical intervention for nerve compression has been reported to improve hand function in individuals with Hurler disease (Van Heest A E et al., 1998, Surgical Treatment of Carpal Tunnel Syndrome and Trigger Digits in Children with Mucopolysaccharide Storage Disorders, J. Hand Surgery 23A, 236-243).

Kolodny et al. have provided a general overview of several approaches for treatment of LSDs in current use or development, including bone marrow transplantation, enzyme replacement therapy, and gene therapy (Kolodny et al., 1998, Id.). However, a need exists for defined combination therapies that overcome significant limitations associated with each of these treatment modalities when used alone. The present invention meets this need by providing approaches utilizing combinations of two or more of enzyme replacement therapy, gene therapy and small molecule therapy.

3. SUMMARY OF THE INVENTION

This invention provides various combinations of enzyme replacement therapy, gene therapy, and small molecule therapy for the treatment of lysosomal storage diseases. According to the invention, several general approaches are provided. Each general approach involves combining at least two of enzyme replacement therapy (ERT), gene therapy (GT), and small molecule therapy (SMT) in a manner which optimizes clinical benefit while minimizing disadvantages associated with using GT or ERT or SMT alone.

Enzyme replacement therapy may be used as a de-bulking strategy (i.e. to initiate treatment), followed by or simultaneously supplemented with gene therapy and/or small molecule therapy. An advantage of ERT, whether used for de-bulking and/or for more long-term care, is the much broader clinical experience available to inform the practitioner's decisions. Moreover, a subject can be effectively titrated with ERT during the de-bulking phase by, for example, monitoring biochemical metabolites in urine or other body samples, or by measuring affected organ volume. A major disadvantage of ERT is the frequency of the administration required, typically involving intravenous injection on a weekly or bi-weekly basis.

Gene therapy may also be administered as an effective method to de-bulk a subject, followed by or supplemented with enzyme replacement therapy and/or small molecule therapy as needed (e.g. when a gene therapy vector immune response precludes further immediate gene therapy, or when a gene therapy vector is administered in low dose to avoid an immune response, and consequently needs supplementation to provide therapeutic enzyme amounts). The major advantage of gene therapy is the prolonged time course of effective treatment which can be achieved. The persistence of the transduced gene is such that therapeutically beneficial enzyme is produced for a duration of from several months to as long as one to several years, or even indefinitely, following a single administration of the gene therapy vector. This low frequency of administration is in stark contrast to enzyme replacement therapy, wherein a recombinantly-produced protein is generally required to be administered on at least a weekly or bi-weekly schedule.

Alternating among GT and ERT and SMT, or supplementing low-dose GT with ERT and/or SMT, provides a strategy for simultaneously taking advantage of the strengths and addressing the weaknesses associated with each therapy employed alone. On one hand, a vector immune response in a subject undergoing gene therapy can be successfully addressed by switching the subject to enzyme replacement therapy until the vector immune response subsides. On the other hand, a subject currently undergoing, for example, a bi-weekly enzyme replacement therapy dosing regimen can be offered an "ERT holiday" (e.g., using a GT administration which is effective for six months or longer, alone or in combination with SMT) wherein frequent enzyme injections are not required therapy.

Accordingly, this invention provides a method of combination therapy for treatment of a subject diagnosed as having a lysosomal storage disease comprising: (a) monitoring the subject for an immune response to a gene therapy; and (b) treating the subject with an enzyme replacement therapy prior to or when the immune response to the gene therapy reaches a parameter determined to be clinically unacceptable.

This invention provides a method of combination therapy for treatment of a subject diagnosed as having a lysosomal storage disease comprising: (a) monitoring the subject for an immune response to a gene therapy; and (b) treating the subject with a small molecule therapy prior to or when the immune response to the gene therapy reaches a parameter determined to be clinically unacceptable.

This invention provides a method of combination therapy for treatment of a subject diagnosed as having a lysosomal storage disease comprising: (a) administering a low dose gene therapy to the subject; (b) monitoring the subject for a disease status indicator in response to the low dose gene therapy; and (c) administering a supplemental enzyme replacement therapy prior to or when the disease status indicator reaches a parameter determined to be clinically unacceptable.

This invention provides a method of combination therapy for treatment of a subject diagnosed as having a lysosomal storage disease comprising: (a) administering a low dose gene therapy to the subject; (b) monitoring the subject for a disease status indicator in response to the low dose gene therapy; and (c) administering a supplemental small molecule therapy prior to or when the disease status indicator reaches a parameter determined to be clinically unacceptable.

This invention provides a method of combination therapy for treatment of a subject diagnosed as having a lysosomal storage disease comprising: (a) administering a low dose gene therapy to the subject; (b) monitoring the subject for a disease status indicator in response to the low dose gene therapy; and (c) simultaneously administering a supplemental enzyme replacement therapy and a small molecule therapy prior to or when the disease status indicator reaches a parameter determined to be clinically unacceptable.

This invention provides a method of combination therapy for treatment of a subject diagnosed as having a lysosomal storage disease comprising: (a) administering a low dose gene therapy to the subject; (b) monitoring the subject for a disease status indicator in response to the low dose gene therapy; and (c) alternating between a supplemental enzyme replacement therapy and a small molecule therapy prior to or when the disease status indicator reaches a parameter determined to be clinically unacceptable.

This invention provides a method of combination therapy for treatment of a subject diagnosed as having a lysosomal storage disease comprising alternating between administration of an enzyme replacement therapy and a gene therapy.

This invention provides a method of combination therapy for treatment of a subject diagnosed as having a lysosomal storage disease comprising alternating between administration of an enzyme replacement therapy and a small molecule therapy.

This invention provides a method of combination therapy for treatment of a subject diagnosed as having a lysosomal storage disease comprising alternating between administration of a gene therapy and a small molecule therapy.

This invention provides a method of combination therapy for treatment of a subject diagnosed as having a lysosomal storage disease comprising alternating between administration of an enzyme replacement therapy, a gene therapy, and a small molecule therapy.

This invention provides a method of combination therapy for treatment of a subject diagnosed as having a lysosomal storage disease comprising alternating between administration of an enzyme replacement therapy, said enzyme replacement therapy being simultaneously administered with a small molecule therapy, and a gene therapy.

This invention provides a method of combination therapy for treatment of a subject diagnosed as having a lysosomal storage disease comprising alternating between administration of an enzyme replacement therapy and a gene therapy, said gene therapy being simultaneously administered with a small molecule therapy.

This invention provides a method of combination therapy for treatment of a subject diagnosed as having a lysosomal storage disease comprising alternating between administration of a small molecule therapy and a gene therapy, said gene therapy being simultaneously administered with an enzyme replacement therapy.

This invention provides a method of combination therapy for treatment of a subject diagnosed as having a lysosomal storage disease comprising alternating between administration of a gene therapy and an enzyme replacement therapy, wherein each of said gene therapy and said enzyme replacement therapy is simultaneously administered with a small molecule therapy.

This invention provides a method of combination therapy for treatment of a subject diagnosed as having a lysosomal storage disease comprising alternating between administration of a gene therapy and a small molecule therapy, wherein each of said gene therapy and said small molecule therapy is simultaneously administered with an enzyme replacement therapy.

This invention provides a method of combination therapy for treatment of a subject diagnosed as having a lysosomal storage disease comprising alternating between administration of an enzyme replacement therapy and a small molecule therapy, wherein each of said enzyme replacement therapy and said small molecule therapy is simultaneously administered with a gene therapy.

This invention provides a method of combination therapy for treatment of a subject diagnosed as having a lysosomal storage disease comprising simultaneously administering a gene therapy and an enzyme replacement therapy.

This invention provides a method of combination therapy for treatment of a subject diagnosed as having a lysosomal storage disease comprising simultaneously administering a gene therapy and a small molecule therapy.

This invention provides a method of combination therapy for treatment of a subject diagnosed as having a lysosomal storage disease comprising simultaneously administering an enzyme replacement therapy and a small molecule therapy.

This invention provides a method of combination therapy for treatment of a subject diagnosed as having a lysosomal storage disease comprising simultaneously administering a gene therapy, an enzyme replacement therapy and a small molecule therapy.

This invention provides a method of combination therapy for treatment of a subject diagnosed as having a lysosomal storage disease comprising: (a) administering an enzyme replacement therapy for a period of at least six months to de-bulk the subject; and (b) administering a gene therapy to the de-bulked subject in order to provide an infusion vacation for a period of at least six months.

This invention provides a method for determining when to substitute repeated administration of gene therapy with enzyme replacement therapy in the treatment of Gaucher's disease in a subject comprising: (a) monitoring an immune status indicator in the subject; (b) administering enzyme replacement therapy in lieu of repeated administration of gene therapy prior to or when the immune status indicator reaches a value determined to be clinically unacceptable. In a preferred embodiment, the enzyme replacement therapy administered in step (b) comprises a dosage regimen of from 2.5 U/kg three times a week to 60 U/kg once every two weeks.

This invention provides a method for determining when to substitute repeated administration of gene therapy with small molecule therapy in the treatment of Gaucher's disease in a subject comprising: (a) monitoring an immune status indicator in the subject (b) administering small molecule therapy in lieu of repeated administration of gene therapy prior to or when the immune status indicator reaches a value determined to be clinically unacceptable.

This invention provides a method for determining when to substitute repeated administration of gene therapy with enzyme replacement therapy in the treatment of Gaucher's disease in a subject comprising: (a) monitoring an immune status indicator in the subject; (b) administering a combination of enzyme replacement therapy and small molecule therapy in lieu of repeated administration of gene therapy prior to or when the immune status indicator reaches a value determined to be clinically unacceptable. In a preferred embodiment, the enzyme replacement therapy administered in step (b) comprises a dosage regimen of from 2.5 U/kg three times a week to 60 U/kg once every two weeks.

This invention provides a method for determining when to substitute repeated administration of gene therapy with enzyme replacement therapy in the treatment of Fabry's disease in a subject comprising: (a) monitoring globotriaosylceramide and pain in the subject; (b) administering enzyme replacement therapy instead of repeated administration of gene therapy prior to or when globotriaosylceramide or pain reaches a value determined to be clinically unacceptable.

This invention provides a method for determining when to substitute repeated administration of gene therapy with small molecule therapy in the treatment of Fabry's disease in a subject comprising: (a) monitoring globotriaosylceramide and pain in the subject; (b) administering small molecule therapy instead of repeated administration of gene therapy prior to or when globotriaosylceramide or pain reaches a value determined to be clinically unacceptable.

This invention provides a method for determining when to substitute repeated administration of gene therapy with small molecule therapy in the treatment of Fabry's disease in a subject comprising: (a) monitoring globotriaosylceramide and pain in the subject (b) administering a combination of small molecule therapy and enzyme replacement therapy instead of repeated administration of gene therapy prior to or when globotriaosylceramide or pain reaches a value determined to be clinically unacceptable.

This invention provides a method for determining when to substitute repeated administration of gene therapy with enzyme replacement therapy in the treatment of Fabry's disease in a subject comprising: (a) monitoring globotriaosylceramide and pain in the subject; (b) administering enzyme replacement therapy instead of repeated administration of gene therapy prior to or when globotriaosylceramide and pain reach values determined to be clinically unacceptable.

This invention provides a method for determining when to substitute repeated administration of gene therapy with small molecule therapy in the treatment of Fabry's disease in a subject comprising: (a) monitoring globotriaosylceramide and pain in the subject; (b) administering small molecule therapy instead of repeated administration of gene therapy prior to or when globotriaosylceramide and pain reach values determined to be clinically unacceptable.

This invention provides a method for determining when to substitute repeated administration of gene therapy with small molecule therapy in the treatment of Fabry's disease in a subject comprising: (a) monitoring globotriaosylceramide and pain in the subject; (b) administering a combination of small molecule therapy and enzyme replacement therapy instead of repeated administration of gene therapy prior to or when globotriaosylceramide and pain reach values determined to be clinically unacceptable.

In the various combination therapies of the invention, it will be understood that administering small molecule therapy may occur prior to, concurrently with, or after, administration of one or more of the other therapies. Similarly, administering enzyme replacement therapy may occur prior to, concurrently with, or after, administration of one or more of the other therapies. Finally, administering gene therapy may occur prior to, concurrently with, or after, administration of one or more of the other therapies.

In any of the foregoing embodiments of the invention, the lysosomal storage disease is selected from the group consisting of Gaucher, Niemann-Pick, Farber, $G_{M1}$-gangliosidosis, $G_{M2}$-gangliosidosis (Sandhoff), Tay-Sachs, Krabbe, Hurler-Scheie (MPS I), Hunter (MPS II), Sanfilippo (MPS III) Type A, Sanfilippo (MPS III) Type B, Sanfilippo (MPS III) Type C, Sanfilippo (MPS III) Type D, Marquio (MPS IV) Type A, Marquio (MPS IV) Type B, Maroteaux-Lamy (MPS VI), Sly (MPS VII), mucosulfatidosis, sialidoses, mucolipidosis II, mucolipidosis III, mucolipidosis IV, Fabry, Schindler, Pompe, sialic acid storage disease, fucosidosis, mannosidosis, aspartylglucosaminuria, Wolman, and neuronal ceroid lipofucsinoses.

Further, the foregoing combination therapies provide an effective amount of at least one enzyme selected from the group consisting of glucocerebrosidase, sphingomyelinase, ceramidase, $G_{M1}$-ganglioside-β-galactosidase, hexosaminidase A, hexosaminidase B, β-galactocerebrosidase, α-L-iduronidase, iduronate sulfatase, heparan-N-sulfatase, N-acetyl-α-glucosaminidase, acetyl CoA:α-glucosaminide acetyltransferase, N-acetyl-α-glucosamine-6-sulfatase, galactosamine-6-sulfatase, β-galactosidase, galactosamine-4-sulfatase (arylsulfatase B), β-glucuronidase, arylsulfatase A, arylsulfatase C, α-neuraminidase, N-acetyl-glucosamine-1-phosphate transferase, α-galactosidase A, α-N-acetylgalactosaminidase, α-glucosidase, α-fucosidase, α-mannosidase, aspartylglucosamine amidase, acid lipase, and palmitoyl-protein thioesterase (CLN-1).

Still further, the foregoing combination therapy produces a diminution in at least one stored material selected from the group consisting of glucocerebroside, sphingomyelin, ceramide, $G_{M1}$-ganglioside, $G_{M2}$-ganglioside, globoside, galactosylceramide, dermatan sulfate, heparan sulfate, keratan sulfate, sulfatides, mucopolysaccharides, sialyloligosaccharides, glycoproteins, sialyloligosaccharides, glycolipids, globotriaosylceramide, O-linked glycopeptides, glycogen, free sialic acid, fucoglycolipids, fucosyloligosaccharides, mannosyloligosaccharides, aspartylglucosamine, cholesteryl esters, triglycerides, and ceroid lipofuscin pigments.

In one embodiment of the invention, the small molecule therapy comprises administering to the subject an effective amount of deoxynojirimycin or a deoxynojirimycin derivative. In another embodiment, the deoxynojirimycin derivative is N-propyldeoxynojirimycin, N-butyldeoxynojirimycin, N-butyldeoxygalactonojirimycin, N-pentyldeoxynojirimycin, N-heptyldeoxynojirimycin, N-pentanoyldeoxynojirimycin, N-(5-adamantane-1-ylmethoxy)pentyl)-deoxynojirimycin, N-(5-cholesteroxypentyl)-deoxynojirimycin, N-(4-adamantanemethanylcarboxy-1-oxo)-deoxynojirimycin, N-(4-adamantanylcarboxy-1-oxo)-deoxynojirimycin, N-(4-phenantrylcarboxy-1-oxo)-deoxynojirimycin, N-(4-cholesterylcarboxy-1-oxo)-deoxynojirimycin, or N-(4-β-cholestanylcarboxy-1-oxo)-deoxynojirimycin.

In another embodiment, the small molecule therapy comprises administering to the subject an effective amount of D-threo-1-phenyl-2-palmitoylamino-3-pyrrolidino-1-propanol (P4) or a P4 derivative. In another embodiment, the P4 derivative is selected from the group consisting of D-threo-4'-hydroxy-1-phenyl-2-palmitoylamino-3-pyrrolidino-1-propanol (4'-hydroxy-P4), D-threo-1-(3',4'-trimethylenedioxy)phenyl-2-palmitoylamino-3-pyrrolidino-1-propanol (trimethylenedioxy-P4), D-threo-1-(3',4'-methylenedioxy)phenyl-2-palmitoylamino-3-pyrrolidino-1-propanol (methylenedioxy-P4) and D-threo-1-(3',4'-ethylenedioxy)phenyl-2-palmitoylamino-3-pyrrolidino-1-propanol (ethylenedioxy-P4 or D-t-et-P4).

In one embodiment of the invention, the lysosomal storage disease is attributable at least in part to a stop codon mutation in a gene encoding a lysosomal storage enzyme, and wherein the small molecule therapy comprises administering to the subject an effective amount of an aminoglycoside. In another embodiment, the aminoglycoside is gentamicin, G418, hygromycin B, paromomycin, tobramycin or Lividomycin A.

In another embodiment, the immune response to gene therapy is monitored by assay of an immune status indicator selected from the group consisting an antibody and a cytokine. In another embodiment, the cytokine is selected from the group consisting of IL-1α, IL-2, IL-4, IL-8, IL-10, G-CSF, GM-CSF, M-CSF, α-interferon, β-interferon and γ-interferon. In another embodiment, the antibody is specifically reactive with an antigen selected from the group consisting of a viral antigen, a lipid antigen and a DNA antigen.

In one preferred embodiment, the lysosomal storage disease has at least one central nervous system manifestation and the small molecule therapy comprises AMP-DNJ.

In the various embodiments of the invention, the subject may be a human or a non-human animal.

4. BRIEF DESCRIPTION OF THE DRAWINGS

Figure 1B:
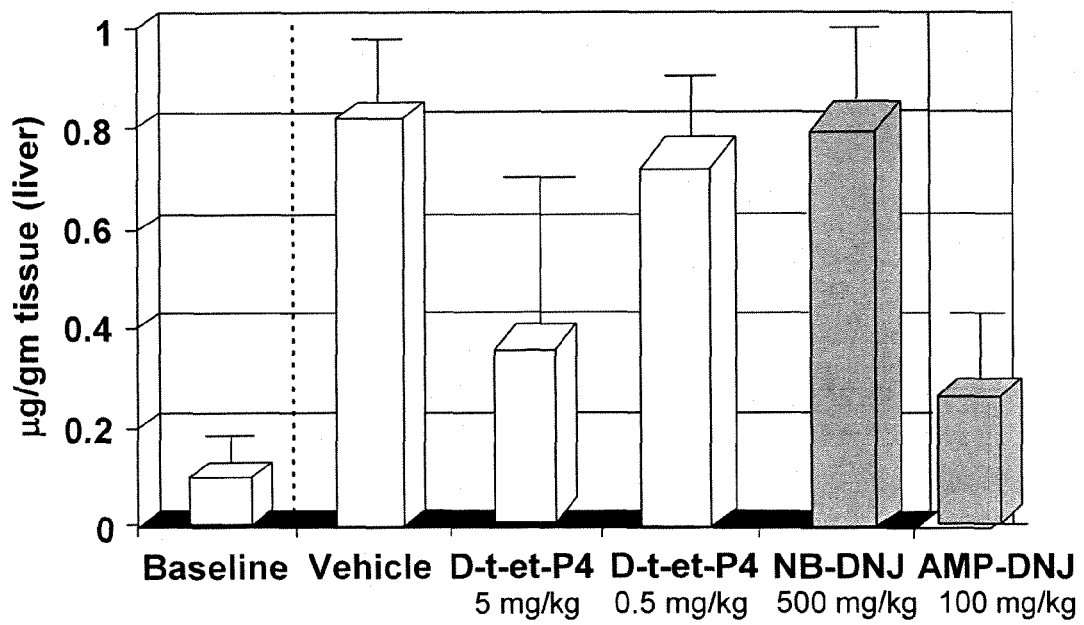

FIG. 1 In vivo efficacy of combination enzyme replacement therapy plus small molecule therapy in Fabry disease. FIG. 1A. Study protocol for sequential combination of enzyme (α-galactosidase A) replacement followed by small molecule administration (NB-DNJ, AMP-DNJ or D-t-et-P4) on globotriaosylceramide (GB3) re-accumulation in Fabry mice. FIG. 1B. Results of study protocol for Fabry mouse liver tissue. GB3 re-accumulation at four weeks (μg GB3 per gm liver tissue) is plotted on the ordinate versus absence of small molecule treatment (Vehicle) or daily intra-peritoneal small molecule therapy with D-t-et-P4 (at either 5 mg/kg or 0.5 mg/kg), NB-DNJ (at 500 mg/kg), or AMP-DNJ (at 100 mg/kg). Baseline GB3 level in Fabry mouse liver (about 0.1 μg/gm liver tissue) shows the GB3 level achieved at two weeks following a single α-galactosidase A intravenous infusion. In control animals receiving daily Vehicle administration, GB3 re-accumulated to about 0.8 μg/gm liver tissue at the four week time point. In marked contrast, D-t-et-P4 (5 mg/kg) and AMP-DNJ (100 mg/kg) reduced GB3 re-accumulation in Fabry mouse liver tissue to less than about 0.4 μg/gm or 0.3 μg/gm, respectively, at the four week time point.

5. DETAILED DESCRIPTION OF THE INVENTION

The therapeutic methods of the invention described herein provide treatment options for the practitioner faced with management of various lysosomal storage diseases, as described in detail below. More specifically, the invention relates to various combinations of enzyme replacement therapy and gene therapy for the treatment of lysosomal storage diseases.

A partial list of known lysosomal storage diseases that can be treated in accordance with the invention is set forth in Table 1, including common disease name, material stored, and corresponding enzyme deficiency (adaptedfrom Table 38-4 of Kolodny et al., 1998, Id.).

TABLE 1

| Lysosomal Storage Diseases | | |
|---|---|---|
| Disease | Material Stored | Enzyme Deficiency |
| Sphingolipidoses | | |
| Gaucher | Glucocerebroside | Glucocerebrosidase |
| Niemann-Pick | Sphingomyelin | Sphingomyelinase |
| Farber | Ceramide | Ceramidase |
| $G_{M1}$-gangliosidosis | $G_{M1}$-ganglioside, glycoprotein | $G_{M1}$-ganglioside-β-galactosidase |
| $G_{M2}$-gangliosidosis (Sandhoff) | $G_{M2}$-ganglioside, globoside | Hexosaminidase A and B |
| Tay-Sachs | $G_{M2}$-ganglioside | Hexosaminidase A |
| Krabbe | Galactosylceramide | β-Galactocerebrosidase |
| Mucopolysaccharidoses | | |
| Hurler-Scheie (MPS I) | Dermatan sulfate, heparan sulfate | α-L-iduronidase |
| Hunter (MPS II) | Dermatan sulfate, heparan sulfate | Iduronate sulfatase |
| Sanfilippo (MPS III) | | |
| Type A | Heparan sulfate | Heparan-N-sulfatase |
| Type B | Heparan sulfate | N-acetyl-α-glucosaminidase |

TABLE 1-continued

Lysosomal Storage Diseases

| Disease | Material Stored | Enzyme Deficiency |
| --- | --- | --- |
| Type C | Heparan sulfate | Acetyl CoA:α-glucosaminide acetyl-transferase |
| Type D | Heparan sulfate | N-acetyl-α-glucosamine-6-sulfatase |
| Marquio (MPS IV) | | |
| Type A | Keratan sulfate | Galactosamine-6-sulfatase |
| Type B | Keratan sulfate | β-galactosidase |
| Maroteaux-Lamy (MPS VI) | Dermatan sulfate | Galactosamine-4-sulfatase (arylsulfatase B) |
| Sly (MPS VII) | Dermatan sulfate, heparan sulfate | β-glucuronidase |
| Mucosulfatidosis | Sulfatides, mucopolysaccharides | Arylsulfatase A, B and C, other sulfatases |
| Mucolipidoses | | |
| Sialidoses | Sialyloligosaccharides, glycoproteins | α-neuraminidase |
| Mucolipidosis II | Sialyloligosaccharides, glycoproteins, glycolipids | High serum, low fibroblast enzymes; N-acetyl-glucosamine-1-phosphate transferase |
| Mucolipidosis III | Glycoproteins, glycolipids | Same as above |
| Mucolipidosis IV | Glycolipids, glycoproteins | Unknown |
| Other Diseases of Complex Carbohydrate Metabolism | | |
| Fabry | Globotriaosylceramide | α-galactosidase A |
| Schindler | O-linked glycopeptides | α-N-acetylgalactosaminidase |
| Pompe | Glycogen | α-glucosidase |
| Sialic acid storage disease | Free sialic acid | Unknown |
| Fucosidosis | Fucoglycolipids, fucosyloligosaccharides | α-fucosidase |
| Mannosidosis | Mannosyloligosaccharides | α-mannosidase |
| Aspartylglucosaminuria | Aspartylglucosamine | Aspartylglucosamine amidase |
| Wolman | Cholesteryl esters, triglycerides | Acid lipase |
| Neuronal ceroid lipofucsinoses | Ceroid lipofuscin pigments | Palmitoyl-protein thioesterase (CLN-1) |

An "effective amount" of an enzyme, small molecule, or gene therapy, when delivered to a subject in a combination therapy of the invention, is an amount sufficient to improve the clinical course of a lysosomal storage disease, where clinical improvement is measured by any of the variety of defined parameters well known to the skilled artisan.

Any method known to the skilled artisan may be used to monitor disease status and the effectiveness of a combination therapy of the invention. Clinical monitors of disease status may include but are not limited to organ volume (e.g. liver, spleen), hemoglobin, erythrocyte count, hematocrit, thrombocytopenia, cachexia (wasting), and plasma chitinase levels (e.g. chitotriosidase). Chitotriosidase, an enzyme of the chitinase family, is known to be produced by macrophages in high levels in subjects with lysosomal storage diseases (see Guo et al., 1995, J. Inherit. Metab. Dis. 18, 717-722; den Tandt et al., 1996, J. Inherit. Metab. Dis. 19, 344-350; Dodelson de Kremer et al., 1997, Medicina (Buenos Aires) 57, 677-684; Czartoryska et al., 2000, Clin. Biochem. 33, 147-149; Czartoryska et al., 1998, Clin. Biochem. 31, 417-420; Mistry et al., 1997, Baillieres Clin. Haematol. 10, 817-838; Young et al., 1997, J. Inherit. Metab. Dis. 20, 595-602; Hollak et al., 1994, J. Clin. Invest. 93, 1288-1292).

Methods and formulations for administering the combination therapies of the invention include all methods and formulations well known in the art (see, e.g., *Remington's Pharmaceutical Sciences*, 1980 and subsequent years, 16th ed. and subsequent editions, A. Oslo editor, Easton Pa.; *Controlled Drug Delivery*, 1987, 2nd rev., Joseph R. Robinson & Vincent H. L. Lee, eds., Marcel Dekker, ISBN: 0824775880; *Encyclopedia of Controlled Drug Delivery*, 1999, Edith Mathiowitz, John Wiley & Sons, ISBN: 0471148288; U.S. Pat. No. 6,066,626 and references cited therein; see also, references cited in sections below).

According to the invention, the following general approaches are provided for combination therapy in the treatment of lysosomal storage diseases. Each general approach involves combining enzyme replacement therapy with gene therapy and/or with small molecule therapy in a manner consistent with optimizing clinical benefit while minimizing disadvantages associated with using each therapy alone.

In a first general approach to a combination therapy of the invention, enzyme replacement therapy (alone or in combination with small molecule therapy) is administered to initiate treatment (ie. to de-bulk the subject), and gene therapy (alone or in combination with small molecule therapy) is administered after the de-bulking phase to achieve and maintain a stable, long-term therapeutic effect without the need for frequent intravenous ERT injections. For example, enzyme replacement therapy may be administered intravenously (e.g. over a one to two hour period) on a weekly or bi-weekly basis for one to several weeks or months, or longer (e.g. until an involved indicator organ such as spleen or liver shows a decrease in size). Moreover, the ERT phase of initial debulking treatment can be performed alone or in combination with a small molecule therapy. After this initial phase, gene therapy may be administered to achieve a prolonged clinical benefit that does not require frequent intravenous intervention. Depending on the nature of the gene therapy vector introduced, the gene therapy component of a combination therapy of the invention optimally will not need supplement for a period of six months, one year, or even indefinitely. An SMT component of a combination therapy can be adjusted as needed throughout the course of the storage disease by the skilled practitioner by monitoring well known clinical signs of disease progression or remission. A small molecule therapeutic component is particularly preferred where the small molecule is compatible with oral administration, thus providing further relief from frequent intravenous intervention.

In a second general approach to a combination therapy of the invention, gene therapy can be administered to de-bulk the subject, followed by or simultaneously supplemented with enzyme replacement therapy and/or small molecule therapy. Such an approach is particularly indicated where a lysosomal storage disease exhibits clinical pathology in an organ having a relatively low circulation (e.g. lymph nodes). In this scenario, deposition and long-term residence of the therapeutic gene by GT at a low-circulation site reduces the dependence of clinical success on repeated IV injections that may have trouble reaching the site. Enzyme replacement therapy and/or small molecule therapy is then used as needed to supplement or maintain the clinical benefit from gene therapy. Moreover, a relatively low dose of gene therapy may be initially employed, e.g. to minimize a vector immune response, supplemented with simultaneous enzyme replacement and/or small molecule therapy as needed to achieve the desired clinical result.

A third general approach to a combination therapy of the invention involves alternative dosing. In one embodiment of alternative dosing, enzyme replacement therapy and/or small molecule therapy may be administered during a period of time required for immune system recovery from an immune response raised against a gene therapy vector. In another embodiment of alternative dosing, gene therapy is administered to provide a prolonged period of time (e.g. six months to one year or longer) wherein weekly or bi-weekly intravenous enzyme infusions are not required (i.e. an "infusion vacation"). Of course, the GT component and the ERT component can each be supplemented with small molecule therapy as needed.

A variety of gene therapy vectors are available for the treatment of the various LSDs (described in detail below). For example, in vivo and ex vivo approaches to gene therapy may be implemented using viral or non-viral vectors. The central nervous system (CNS) is generally much harder to target than the reticuloendothelial system (RES) because of the blood-brain barrier (BBB). However, bone marrow cells transduced to express a therapeutic gene may provide some CNS benefit. Finally, cationic-lipid-plus-plasmid combinations are especially indicated for diseases that have lung involvement since they can, for example, be administered by aerosol at the disease locus.

Gene therapy and enzyme replacement therapy can provoke unwanted immune responses. Accordingly, immunosuppressant agents may be used together with a gene therapy component or an enzyme replacement therapy component of a combination therapy of the invention. Such agents may also be used with a small molecule therapy component, but the need for intervention here is generally less likely. Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor ($\alpha$-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Any combination of immunosuppressant agents known to the skilled artisan can be used together with a combination therapy of the invention. One immunosuppressant agent combination of particular utility is tacrolimus (FK506) plus sirolimus (rapamycin) plus daclizumab (anti-IL2 receptor $\alpha$-subunit antibody). This combination is proven effective as an alternative to steroids and cyclosporine, and when specifically targeting the liver. Moreover, this combination has recently been shown to permit successful pancreatic islet cell transplants. See Denise Grady, The New York Times, Saturday, May 27, 2000, pages A1 and A11. See also A. M. Shapiro et al., Jul. 27, 2000, "Islet Transplantation In Seven Patients With Type 1 Diabetes Mellitus Using A Glucocorticoid-Free Immunosuppressive Regimen", N. Engl. J. Med. 343, 230-238; Ryan et al., 2001, Diabetes 50, 710-719. Plasmaphoresis by any method known in the art may also be used to remove or deplete antibodies that may develop against various components of a combination therapy.

Immune status indicators of use with the invention include but are not limited to antibodies and any of the cytokines known to the skilled artisan, e.g., the interleukins, CSFs and interferons (see generally, Leonard et al., 2000, J. Allergy Clin. Immunol. 105, 877-888; Oberholzer et al., 2000, Crit. Care Med. 28 (4 Suppl.), N3-N12; Rubinstein et al., 1998, Cytokine Growth Factor Rev. 9, 175-181). For example, antibodies specifically immunoreactive with the replacement enzyme or vector components can be monitored to determine immune status of the subject. Among the two dozen or so interleukins known, particularly preferred immune status indicators are IL-1$\alpha$, IL-2, IL-4, IL-8 and IL-10. Among the colony stimulating factors (CSFs), particularly preferred immune status indicators are G-CSF, GM-CSF and M-CSF. Among the interferons, one or more alpha, beta or gamma interferons are preferred as immune status indicators.

In Sections 5.1 through 5.8 which follow, various components which may be used for eight specific lysosomal storage diseases are provided (i.e. Gaucher, Fabry, Niemann-Pick B, Hunter, Morquio, Maroteaux-Lamy, Pompe, and Hurler-Scheie). In Section 5.9 and subsequent sections, further enabling disclosure for gene therapy, enzyme replacement therapy, and small molecule therapy components of a combination therapy of the invention are provided.

5.1 Gaucher

As noted above, Gaucher's disease is caused by inactivation of the enzyme glucocerebrosidase (β-D-glucosyl-N-acylsphingosine glucohydrolase, EC 3.2.1.45) and accumulation of glucocerebroside (glucosylceramide). For an enzyme replacement therapy component of a combination therapy of the invention for the treatment of Gaucher's disease, a number of references are available which set forth satisfactory dosage regimens and other useful information relating to treatment (see Morales, 1996, Gaucher's Disease: A Review, The Annals of Pharmacotherapy 30, 381-388; Rosenthal et al., 1995, Enzyme Replacement Therapy for Gaucher Disease: Skeletal Responses to Macrophage-targeted Glucocerebrosidase, Pediatrics 96, 629-637; Barton et al., 1991, Replacement Therapy for Inherited Enzyme Deficiency—Macrophage-targeted Glucocerebrosidase for Gaucher's Disease, New England Journal of Medicine 324, 1464-1470; Grabowski et al., 1995, Enzyme Therapy in Type 1 Gaucher Disease: Comparative Efficacy of Mannose-terminated Glucocerebrosidase from Natural and Recombinant Sources, Annals of Internal Medicine 122, 33-39; Pastores et al., 1993, Enzyme Therapy in Gaucher Disease Type 1: Dosage Efficacy and Adverse Effects in 33 Patients treated for 6 to 24 Months, Blood 82, 408-416).

In one embodiment, an ERT dosage regimen of from 2.5 units per kilogram (U/kg) three times a week to 60 U/kg once every two weeks is provided, where the enzyme is administered by intravenous infusion over 1-2 hours. A unit of glucocerebrosidase is defined as the amount of enzyme that catalyzes the hydrolysis of one micromole of the synthetic substrate para-nitrophenyl-p-D-glucopyranoside per minute at 37° C. In another embodiment, a dosage regimen of from 1 U/kg three times a week to 120 U/kg once every two weeks is provided. In yet another embodiment, a dosage regimen of from 0.25 U/kg daily or three times a week to 600 U/kg once every two to six weeks is provided.

Since 1991, aglucerase (Ceredase™) has been available from Genzyme Corporation. Aglucerase is a placentally-derived modified form of glucocerebrosidase. In 1994, imiglucerase (Cerezyme™) also became available from Genzyme Corporation. Imiglucerase is a modified form of glucocerebrosidase derived from expression of recombinant DNA in a mammalian cell culture system (Chinese hamster ovary cells). Imiglucerase is a monomeric glycoprotein of 497 amino acids containing four N-linked glycosylation sites. Imiglucerase has the advantages of a theoretically unlimited supply and a reduced chance of biological contaminants relative to placentally-derived aglucerase. oth enzymes are modified at their glycosylation sites to expose mannose residues, a maneuver which improves lysosomal targeting via the mannose-6-phosphate receptor. Imiglucerase differs from placental glucocerebrosidase by one amino acid at position 495 where histidine is substituted for arginine. Several dosage regimens of these products are known to be effective (see Morales, 1996, Id.; Rosenthal et al., 1995, Id.; Barton et al., 1991, Id.; Grabowski et al., 1995, Id.; Pastores et al., 1993, Id.). For example, a dosage regimen of 60 U/kg once every two weeks is of clinical benefit in subjects with moderate to severe disease. The references cited above and the package inserts for these products should be consulted by the skilled practitioner for additional dosage regimen and administration information. See also U.S. Pat. Nos. 5,236,838 and 5,549,892 assigned to Genzyme Corporation.

For a small molecule therapy component of a combination therapy of the invention for the treatment of Gaucher's disease, Cox and colleagues provide specific guidance regarding satisfactory dosage regimens and other useful information relating to oral treatment with N-butyldeoxynojirimycin (NB-DNJ) in Gaucher's disease (Cox et al., 2000, Lancet 355, 1481-1485). Additional guidance is provided by the following references relating to various deoxynojirimycin (DNJ)—like compounds: Jeyakumar et al., 2001, Blood 97, 327-329 (NB-DNJ therapy plus bone marrow transplantation); Andersson et al., 2000, Biochem. Pharmacol. 59, 821-829 (N-butyldeoxygalactonojirimycin as a more selective inhibitor than NB-DNJ); Jeyakumar et al., 1999, Proc. Natl. Acad. Sci. USA 96, 6388-6393 (NB-DNJ for treatment of glycosphingolipid storage diseases having a CNS component); and Platt et al., 1997, Science 276, 428-431 (CNS benefit using NB-DNJ to achieve substrate deprivation).

5.2 Fabry

As noted previously, Fabry's disease is caused by inactivation of the lysosomal enzyme alpha-galactosidase A. The enzymatic defect leads to systemic deposition of glycosphingolipids having terminal alpha-galactosyl moieties, predominantly globotriaosylceramide (GL-3 or GL3, see FIG. 1) and, to a lesser extent, galabiosylceramide and blood group B glycosphingolipids.

Several assays are available to monitor disease progression and to determine when to switch from one treatment modality to another. In one embodiment, an assay to determine the specific activity of alpha-galactosidase A in a tissue sample may be used. In another embodiment, an assay to determine the accumulation of GL-3 may be used. In another embodiment, the practitioner may assay for deposition of glycosphingolipid substrates in body fluids and in lysosomes of vascular endothelial, perithelial and smooth muscle cells of blood vessels. Other clinical manifestations which may be useful indicators of disease management include proteinuria, or other signs of renal impairment such as red cells or lipid globules in the urine, and elevated erythrocyte sedimentation rate. One can also monitor anemia, decreased serum iron concentration, high concentration of beta-thromboglobulin, and elevated reticulocyte counts or platelet aggregation. Indeed, any approach for monitoring disease progression which is known to the skilled artisan may be used (See generally Desnick RJ et al., 1995, α-Galactosidase A Deficiency: Fabry Disease, In: The Metabolic and Molecular Bases of Inherited Disease, Scriver et al., eds., McGraw-Hill, N.Y., 7$^{th}$ ed., pages 2741-2784).

A preferred surrogate marker is pain for monitoring Fabry disease management. Other preferred methods include the measurement of total clearance of the enzyme and/or substrate from a bodily fluid or biopsy specimen.

A preferred dosage regimen for enzyme replacement therapy in Fabry disease is 1-10 mg/kg i.v. every other day. A dosage regimen from 0.1 to 100 mg/kg i.v. at a frequency of from every other day to once weekly or every two weeks can be used.

In a preferred embodiment, alpha-galactosidase A is provided in Fabry disease using the recombinant viral and/or non viral vectors described in U.S. Pat. No. 6,066,626.

5.3 Niemann-Pick B

As previously noted, Niemann-Pick B disease is caused by reduced activity of the lysosomal enzyme sphingomyelinase and accumulation of membrane lipid, primarily sphingomyelin. An effective dosage of replacement sphingomyelinase to be delivered may range from about 1 to about 10 mg/kg body weight at a frequency of from every other day to weekly or bi-weekly.

5.4 Hunter

Hunter's disease (a.k.a. MPS II) is caused by inactivation of iduronate sulfatase and accumulation of dermatan sulfate and heparan sulfate. Hunter's disease presents clinically in severe and mild forms.

A dosage regimen of therapeutic enzyme from 1.5 mg/kg every two weeks to 50 mg/kg every week is preferred.

5.5 Morquio

Morquio's syndrome (a.k.a. MPS IV) results from accumulation of keratan sulfate due to inactivation of either of two enzymes. In MPS IVA the inactivated enzyme is galactosamine-6-sulfatase and in MPS IVB the inactivated enzyme is beta-galactosidase.

A dosage regimen of therapeutic enzyme from 1.5 mg/kg every two weeks to 50 mg/kg every week is preferred.

5.6 Maroteaux-Lamy

Maroteaux-Lamy syndrome (a.k.a. MPS VI) is caused by inactivation of alactosamine-4-sulfatase (arylsulfatase B) and accumulation of dermatan sulfate.

A dosage regimen of from 1.5 mg/kg every two weeks to 50 mg/kg every eek is a preferred range of effective therapeutic enzyme provided by ERT. Optimally, the osage employed is less than or equal to 10 mg/kg per week.

A preferred surrogate marker for MPS VI disease progression is roteoglycan levels.

5.7 Pompe

Pompe's disease is caused by inactivation of the acid alpha-glucosidase enzyme and accumulation of glycogen. The acid alpha-glucosidase gene resides on human chromosome 17 and is designated GAA. H. G. Hers first proposed the concept of inborn lysosomal disease based on his studies of this disease, which he referred to as type II glycogen storage disease (GSD II) and which is now also termed acid maltase deficiency (AMD) (see Hers, 1965, Gastroenterology 48, 625).

Several assays are available to monitor Pompe disease progression. Any assay known to the skilled artisan may be used. For example, one can assay for intra-lysosomal accumulation of glycogen granules, particularly in myocardium, liver and skeletal muscle fibers obtained from biopsy. Alpha-glucosidase enzyme activity can also be monitored in biopsy specimens or cultured cells obtained from peripheral blood. Serum elevation of creatine kinase (CK) can be monitored as an indication of disease progression. Serum CK can be elevated up to ten-fold in infantile-onset patients and is usually elevated to a lesser degree in adult-onset patients. See Hirschhorn R, 1995, Glycogen Storage Disease Type II: Acid a-Glucosidase (Acid Maltase) Deficiency, In: The Metabolic and Molecular Bases of Inherited Disease, Scriver et al., eds., McGraw-Hill, N.Y., 7$^{th}$ ed., pages 2443-2464.

5.8 Hurler-Scheie

Hurler, Scheie, and Hurler-Scheie disease, also known as MPS I, are caused by inactivation of alpha-iduronidase and accumulation of dermatan sulfate and heparan sulfate.

Several assays are available to monitor MPS I disease progression. For example, alpha-iduronidase enzyme activity can be monitored in tissue biopsy specimens or cultured cells obtained from peripheral blood. In addition, a convenient measure of disease progression in MPS I and other mucopolysaccharidoses is the urinary excretion of the glycosaminoglycans dermatan sulfate and heparan sulfate (see Neufeld et al., 1995, Id.).

5.9 Gene Therapy

One of the most frequently used methods for administration of gene therapy, both in vivo and ex vivo, is the use of viral vectors for delivery of the gene. Many species of virus are known, and many have been extensively studied for gene therapy purposes. The most commonly used viral vectors include those derived from adenovirus, adeno-associated virus (AAV) and retrovirus, including lentivirus such as human immunodeficiency virus (HIV). See also WO 99/57296 and WO 99/41399.

Among adenovirus, pseudoadenovirus (PAV or gutless adenovirus) is a particularly preferred vector (see below). In this group of vectors, a titre range of from $10^9$ to $10^{13}$ particles per kg body weight is preferred for administration to a subject. For AAV, a titre range of from $10^9$ to $10^{14}$ particles per kg body weight is preferred for administration to a subject. For lentivirus, a titre range of from $10^6$ to $10^{10}$ particles per kg body weight is preferred for administration to a subject. In each instance, the exact titre is determined by adjusting the titre to the amount necessary to deliver an effective amount of enzyme.

5.9.1 Adenovirus

Adenoviral vectors for use to deliver transgenes to cells for various applications, such as in vivo gene therapy and in vitro study and/or production of the products of transgenes, are commonly derived from adenoviruses by deletion of the early region 1 (E1) genes (Berkner, K. L., 1992, Curr. Top. Micro. Immunol. 158, 39-66). Deletion of E1 genes renders such adenoviral vectors replication defective and significantly reduces expression of the remaining viral genes present within the vector. However, it is believed that the presence of the remaining viral genes in adenoviral vectors can be deleterious to the transfected cell for one or more of the following reasons: (1) stimulation of a cellular immune response directed against expressed viral proteins; (2) cytotoxicity of expressed viral proteins; and (3) replication of the vector genome leading to cell death.

One solution to this problem has been the creation of adenoviral vectors with deletions of various adenoviral gene sequences. In particular, pseudoadenoviral vectors (PAVs), also known as 'gutless adenovirus' or mini-adenoviral vectors, are adenoviral vectors derived from the genome of an adenovirus that contain minimal cis-acting nucleotide sequences required for the replication and packaging of the vector genome and which can contain one or more transgenes (see, U.S. Pat. No. 5,882,877 by Gregory et al. which covers pseudoadenoviral vectors (PAV) and methods for producing PAV). Such PAVs, which can accommodate up to about 36 kb of foreign nucleic acid, are advantageous because the carrying capacity of the vector is optimized while the potential for host immune responses to the vector or the generation of replication-competent viruses is reduced. PAV vectors contain the 5' inverted terminal repeat (ITR) and the 3' ITR nucleotide sequences that contain the origin of replication, and the cis-acting nucleotide sequence required for packaging of the PAV genome, and can accommodate one or more transgenes with appropriate regulatory elements, e.g. promoters, enhancers, etc.

Adenoviral vectors, such as PAVs, have been designed to take advantage of the desirable features of adenovirus which render it a suitable vehicle for delivery of nucleic acids to recipient cells. Adenovirus is a non-enveloped, nuclear DNA virus with a genome of about 36 kb, which has been well-characterized through studies in classical genetics and molecular biology (Hurwitz, M. S., *Adenoviruses, Virology*, 3rd edition, Fields et al., eds., Raven Press, New York, 1996; Hitt, M. M. et al., *Adenovirus Vectors, The Development of Human Gene Therapy*, Friedman, T. ed., Cold Spring Harbor Laboratory Press, New York, 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemagglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39-66, 1992; Jolly, D., *Cancer Gene Therapy* 1:51-64, 1994).

PAVs have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 by Gregory et al.; Kochanek et al., *Proc. Natl. Acad. Sci. USA* 93:5731-5736, 1996; Parks et al., *Proc. Natl. Acad. Sci. USA* 93:13565-13570, 1996; Lieber et al., *J. Virol.* 70:8944-8960, 1996; Fisher et al., *Virology* 217:11-22, 1996; U.S. Pat. No. 5,670,488; PCT Publication No. WO 96/33280, published Oct. 24, 1996; PCT Publication No. WO 96/40955, published Dec. 19, 1996; PCT Publication No. WO 97/25446, published Jul. 19, 1997; PCT Publication No. WO 95/29993, published Nov. 9, 1995; PCT Publication No. WO 97/00326, published Jan. 3, 1997; Morral et al., *Hum. Gene Ther.* 10:2709-2716, 1998.

Since PAVs are deleted for most of the adenovirus genome, production of PAVs requires the furnishing of adenovirus proteins in trans which facilitate the replication and packaging of a PAV genome into viral vector particles. Most commonly, such proteins are provided by infecting a producer cell with a helper adenovirus containing the genes encoding such proteins. However, such helper viruses are potential sources of contamination of a PAV stock during purification and can pose potential problems when administering the PAV to an individual if the contaminating helper adenovirus can replicate and be packaged into viral particles.

Accordingly, it is advantageous to increase the purity of a PAV stock by reducing or eliminating any production of helper vectors which can contaminate preparation. Several strategies to reduce the production of helper vectors in the preparation of a PAV stock are disclosed in U.S. Pat. No. 5,882,877, issued Mar. 16, 1999; U.S. Pat. No. 5,670,488, issued Sep. 23, 1997 and International Patent Application No. PCT/US99/03483. For example, the helper vector may contain: (a) mutations in the packaging sequence of its genome to prevent its packaging; (b) an oversized adenoviral genome which cannot be packaged due to size constraints of the virion; or (c) a packaging signal region with binding sequences that prevent access by packaging proteins to this signal which thereby prevents production of the helper virus. Other strategies include the design of a helper virus with a packaging signal flanked by the excision target site of a recombinase, such as the Cre-Lox system (Parks et al., *Proc. Natl. Acad. Sci. USA* 93:13565-13570, 1996; Hardy et al., *J Virol.* 71:1842-1849, 1997). Such helper vectors reduce the yield of wild-type levels.

The use of adenoviruses for gene therapy is described, for example, in U.S. Pat. Nos. 6,040,174; 5,882,877; 5,824,544; 5,707,618; and 5,670,488.

5.9.2 Adeno-Associated Virus (AAV)

Adeno-associated virus (AAV) is a single-stranded human DNA parvovirus hose genome has a size about of 4.6 kb. The AAV genome contains two major genes: the ep gene, which codes for the rep proteins (Rep 76, Rep 68, Rep 52 and Rep 40) and the cap gene, which codes for AAV structural proteins (VP-1, VP-2 and VP-3). The rep proteins are involved in AAV replication, rescue, transcription and integration, while the cap proteins form the AAV viral particle. AAV derives its name from its dependence on an adenovirus or other helper virus (e.g., herpesvirus) to supply essential gene products that allow AAV to undergo a productive infection, i.e., reproduce itself in the host cell. In the absence of helper virus, AAV integrates as a provirus into the host cell's chromosome, until it is rescued by superinfection of the host cell with a helper virus, usually adenovirus (Muzyczka, 1992, Curr. Top. Micro. Immunol. 158, 97-127).

Utility of AAV as a gene transfer vector results from several unique features of its biology. At both ends of the AAV genome is a nucleotide sequence, known as an inverted terminal repeat (ITR), which contains the cis-acting nucleotide sequences required for virus replication, rescue, packaging and integration. The integration function of the ITR mediated by the rep protein in trans permits the AAV genome to integrate into a cellular chromosome after infection, in the absence of helper virus. This unique property of the virus has relevance to the use of AAV in gene transfer, as it allows for integration of a recombinant AAV (rAAV) containing a gene of interest into the cellular genome. Therefore, stable genetic transformation, ideal for many of the goals of gene transfer, may be achieved by use of rAAV vectors. Furthermore, the site of integration for AAV is well-established and has been localized to chromosome 19 of humans (Kotin et al., Proc. Natl. Acad. Sci. 87:2211-2215, 1990). This predictability of integration site reduces the danger of random insertional events into the cellular genome that may activate or inactivate host genes or interrupt coding sequences, consequences that can limit the use of vectors whose integration is random, e.g., retroviruses. However, because the rep protein mediates the integration of AAV, removal of this gene in the design of rAAV vectors may result in the altered integration patterns that have been observed with rAAV vectors (Ponnazhagan et al., Hum. Gene Ther. 8:275-284, 1997).

There are other advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Standard approaches to the generation of recombinant AAV vectors have required the coordination of a series of intracellular events: transfection of the host cell with an rAAV vector genome containing a transgene of interest flanked by the AAV ITR sequences, transfection of the host cell by a plasmid encoding the genes for the AAV rep and cap proteins which are required in trans, and infection of the transfected cell with a helper virus to supply the non-AAV helper functions required in trans (Muzyczka, N., Curr. Top. Micro. Immunol. 158: 97-129, 1992). The adenoviral (or other helper virus) proteins activate transcription of the AAV rep gene, and the rep proteins then activate transcription of the AAV cap genes. The cap proteins then utilize the ITR sequences to package the rAAV genome into an rAAV viral particle. Therefore, the efficiency of packaging is determined, in part, by the availability of adequate amounts of the structural proteins, as well as by the accessibility of any cis-acting packaging sequences required in the rAAV vector genome.

One of the potential limitations to high level rAAV production derives from limiting quantities of the AAV helper proteins required in trans for replication and packaging of the rAAV genome. Some approaches to increasing the levels of these proteins have included the following: placing the AAV rep gene under the control of the HIV LTR promoter to increase rep protein levels (Flotte, F. R. et al., Gene Therapy 2:29-37, 1995); the use of other heterologous promoters to increase expression of the AAV helper proteins, specifically the cap proteins (Vincent et al., J. Virol. 71:1897-1905, 1997); and the development of cell lines that specifically express the rep proteins (Yang, Q. et al., J. Virol. 68: 4847-4856, 1994).

Other approaches to improving the production of rAAV vectors include the use of helper virus induction of the AAV helper proteins (Clark et al., Gene Therapy 3:1124-1132, 1996) and the generation of a cell line containing integrated copies of the rAAV vector and AAV helper genes so that infection by the helper virus initiates rAAV production (Clark et al., Human Gene Therapy 6:1329-1341, 1995). rAAV vectors have been produced using replication-defective helper adenoviruses which contain the nucleotide sequences encoding the rAAV vector genome (U.S. Pat. No. 5,856,152 issued Jan. 5, 1999) or helper adenoviruses which contain the nucleotide sequences encoding the AAV helper proteins (PCT International Publication W095/06743, published Mar. 9, 1995). Production strategies which combine high level expression of the AAV helper genes and the optimal choice of cis-acting nucleotide sequences in the rAAV vector genome have been described (PCT International Application No. WO97/09441 published Mar. 13, 1997).

Current approaches to reducing contamination of rAAV vector stocks by helper viruses, therefore, involve the use of temperature-sensitive helper viruses (Ensinger et al., J. Virol. 10:328-339, 1972), which are inactivated at the non-permissive temperature. Alternatively, the non-AAV helper genes can be subcloned into DNA plasmids which are transfected into a cell during rAAV vector production (Salvetti et al., Hum. Gene Ther. 9:695-706, 1998; Grimm et al., Hum. Gene Ther. 9:2745-2760, 1998).

The use of AAV for gene therapy is described, for example, in U.S. Pat. Nos. 5,753,500 and 5,962,313.

5.9.3 Retrovirus

Retrovirus vectors are a common tool for gene delivery (Miller, 1992, Nature 357, 455-460). The ability of retrovirus vectors to deliver an un-rearranged, single copy gene into a broad range of rodent, primate and human somatic cells makes retroviral vectors well suited for transferring genes to a cell.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

Another useful tool for producing recombinant retroviral vectors is a packaging cell line which supplies in trans the proteins necessary for producing infectious virions but which is incapable of packaging endogenous viral genomic nucleic acids (Watanabe and Temin, 1983, Molec. Cell. Biol. 3(12): 2241-2249; Mann et al., 1983, Cell 33:153-159; Embretson and Temin, 1987, J. Virol. 61(9):2675-2683). One approach to minimize the likelihood of generating replication competent retrovirus (RCR) in packaging cells is to divide the packaging functions into two genomes. For example, one genome may be used to express the gag and pol gene products and the other to express the env gene product (Bosselman et al., 1987, Molec. Cell. Biol. 7(5):1797-1806; Markowitz et al., 1988, J. Virol. 62(4):1120-1124; Danos and Mulligan, 1988, Proc. Natl. Acad. Sci. 85:6460-6464). This approach minimizes the possibility that co-packaging and subsequent transfer of the two genomes will occur; it also significantly decreases the frequency of recombination to produce RCR due to the presence of three retroviral genomes in the packaging cell.

In the event recombinants arise, mutations (Danos and Mulligan, 1988, Id.) or deletions (Bosselman et al., 1987, Id.; Markowitz et al., 1988, Id.) can be configured within the undesired gene products to render any possible recombinants non-functional. In addition, deletion of the 3' LTR on both packaging constructs further reduces the ability to form functional recombinants.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins.

Lentiviruses are complex retroviruses which, in addition to the common retroviral genes gag, pol and env, contain other genes with regulatory or structural function. For example, lentiviruses may have additional genes including vit, vpr, tat, rev, vpu, nef, and vpx. The higher complexity enables the lentivirus to modulate the life cycle, as in the course of latent infection. A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein.

The use of retroviruses for gene therapy is described, for example, in U.S. Pat. Nos. 6,013,516 and 5,994,136.

5.9.4 Non-Viral Vectors

Additional methods for delivery of DNA to cells do not use viruses for delivery. Such methods include the use of compounds such as cationic amphiphilic compounds, non-viral ex vivo transfection, as well as DNA in the absence of viral or non-viral compounds, known as "naked DNA."

Because compounds designed to facilitate intracellular delivery of biologically active molecules must interact with both non-polar and polar environments (in or on, for example, the plasma membrane, tissue fluids, compartments within the cell, and the biologically active molecule itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiologic pH, and this property is understood in the art to be important in defining how the amphiphiles interact with the many types of biologically active (therapeutic) molecules including, for example, negatively charged polynucleotides such as DNA.

Examples of cationic amphiphilic compounds that have both polar and non-polar domains and that are stated to be useful in relation to intracellular delivery of biologically active molecules are found, for example, in the following references, which references also contain useful discussion of (1) the properties of such compounds that are understood in the art as making them suitable for such applications, and (2) the nature of the structures, as understood in the art, that are formed by complexing of such amphiphiles with therapeutic molecules intended for intracellular delivery. Felgner, et al., Proc. Natl. Acad.

Sci. USA, 84, 7413-7417 (1987) disclose use of positively-charged synthetic cationic lipids including N-[1(2,3-dioleyloxy)propyl]-N,N,N-trimethylammonium chloride ("DOTMA"), to form lipid/DNA complexes suitable for transfections. See also Felgner et al., 1994, J. Biol. Chem. 269, 2550-2561. Behr et al., Proc. Natl. Acad. Sci. USA, 86, 6982-6986 (1989) disclose numerous amphiphiles including dioctadecylamidologlycylspermine ("DOGS"). U.S. Pat. No. 5,283,185 to Epand et al. describes additional classes and species of amphiphiles including 3β[N-($N^1$,$N^1$-dimethylaminoethane)-carbamoyl]cholesterol, termed "DC-chol". Additional compounds that facilitate transport of biologically active molecules into cells are disclosed in U.S. Pat. No. 5,264,618 to Felgner et al. See also Felgner et al., 1994, J. Biol. Chem. 269, 2550-2561, for disclosure therein of further compounds including "DMRIE" or 1,2-dimyristyloxypropyl-3-dimethyl-hydroxyethyl ammonium bromide. Reference to amphiphiles suitable for intracellular delivery of biologically active molecules is also found in U.S. Pat. No. 5,334,761 to Gebeyehu et al., and in Felgner et al., 1993, Meth. Enzymol. 5, 67-75.

The use of compositions comprising cationic amphiphilic compounds for gene delivery is described, for example, in U.S. Pat. Nos. 5,049,386; 5,279,833; 5,650,096; 5,747,471; 5,757,471; 5,767,099; 5,910,487; 5,719,131; 5,840,710; 5,783,565; 5,925,628; 5,912,239; 5,942,634; 5,948,925; 6,022,874; 5,994,317; 5,861,397; 5,952,916; 5,948,767; 5,939,401; and 5,935,936.

Another approach to gene therapy is the non-viral transfection ex vivo of a primary or secondary host cell derived from a subject to be treated with a DNA construct carrying the therapeutic gene. Host cells engineered in this way are then re-introduced into the subject to administer the gene therapy. See e.g. U.S. Pat. Nos. 5,994,127; 6,048,524; 6,048,724; 6,048,729; 6,054,288; and 6,063,630.

Methods for delivering a non-infectious, non-integrating DNA sequence encoding a desired polypeptide or peptide operably linked to a promoter, free from association with transfection-facilitating proteins, viral particles, liposomal formulations, charged lipids and calcium phosphate precipitating agents, is described in U.S. Pat. Nos. 5,580,859; 5,963, 622; and 5,910,488.

Gene transfer systems that combine viral and nonviral components have been 20 developed. See Cristiano et al., 1993, Proc. Natl. Acad. Sci. USA 90, 11548; Wu et al., 1994, J. Biol. Chem. 269, 11542; Wagner et al., 1992, Proc. Natl. Acad. Sci. USA 89, 6099; Yoshimura et al., 1993, J. Biol. Chem. 268, 2300; Curiel et al., 1991, Proc. Natl. Acad. Sci USA 88, 8850; Kupfer et al., 1994, Hum. Gene Ther. 5, 1437; and Gottschalk et al., 1994, Gene Ther. 1, 185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes.

5.9.5 Regulated Gene Expression

A number of systems are available to provide regulated expression of a gene delivered to a subject. Any such system known to the skilled artisan may be used in a combination therapy of the invention. Examples of such systems include but are not limited to tet-regulated vectors (see e.g. U.S. Pat. Nos. 6,004,941 and 5,866,755), RU486 gene regulation technology (see U.S. Pat. Nos. 5,874,534 and 5,935,934), and modified FK506 gene regulation technology (see U.S. Pat. Nos. 6,011,018; 5,994,313; 5,871,753; 5,869,337; 5,834,266; 5,830,462; WO 96/41865; and WO 95/33052).

5.10 Enzyme Replacement Therapy

The following sections set forth specific disclosure and alternative embodiments available for the enzyme replacement therapy component of a combination therapy of the invention.

Generally, dosage regimens for an enzyme replacement therapy component of a combination therapy of the invention are generally determined by the skilled clinician. Several examples of dosage regimens for the treatment of Gaucher's disease with lucocerebrosidase were provided above in Section 5.2. The general principles for determining a dosage regimen for any given ERT component of a combination therapy of the invention for the treatment of any LSD will be apparent to the skilled artisan from a eview of the specific references cited in the sections which set forth the enabling information for each specific LSD.

Any method known in the art may be used for the manufacture of the enzymes to be used in an enzyme replacement therapy component of a combination therapy of the invention. Many such methods are known and include but are not limited to the Gene Activation technology developed by Transkaryotic Therapies, Inc. (see U.S. Pat. Nos. 5,968,502 and 5,272, 071).

5.11 Small Molecule Therapy

The following section sets forth specific disclosures and alternative embodiments available for the small molecule therapy component of a combination therapy of the invention. Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT component of any combination therapy of the invention for the treatment of any storage disease are well known to the skilled artisan. Guidance for dosage regimens can be obtained from any of the many well known references in the art on this topic. Further guidance is available, inter alia, from a review of the specific references cited herein.

Generally, substrate deprivation inhibitors such as DNJ-type inhibitors and amino ceramide-like compounds (including P4-type inhibitors) may be used in the combination therapies of the invention for treatment of virtually any storage disease resulting from a lesion in the glycosphingolipid pathway (e.g. Gaucher, Fabry, Sandhoff, Tay-Sachs, $G_{M1}$-gangliosidosis). Likewise, aminoglycosides (e.g. gentamicin, G418) may be used in the combination therapies of the invention for any storage disease individual having a premature stop-codon mutation. Such mutations are particularly prevalent in Hurler syndrome. A small molecule therapy component of a combination therapy of the invention is particularly preferred where there is a central nervous system manifestation to the storage disease being treated (e.g. Sandhoff, Tay-Sachs, Niemann-Pick Type A), since small molecules can generally cross the blood-brain barrier with ease when compared to other therapies. Moreover, derivatives of the small molecules set forth herein are provided, wherein the derivatives have been designed by any method known in the art to facilitate or enhance crossing the blood-brain barrier.

Accordingly, this invention provides small molecule therapy in combination with enzyme replacement therapy and/or gene therapy for treatment of storage diseases. Small molecules useful in the combination therapies of the invention may include but are not limited to those described by Shayman and coworkers, by Aerts and coworkers, and by Bedwell and coworkers in the references cited below.

Examples of amino ceramide-like compounds useful in the combination therapies of the invention may include but are not limited to those described in the following references: Abe et al., 2000, J. Clin. Invest. 105, 1563-1571; Abe et al., 2000, Kidney Int'l 57, 446-454; Lee et al., 1999, J. Biol. Chem. 274, 14662-14669; Shayman et al., 2000, Meth. Enzymol. 31, 373-387; U.S. Pat. Nos. 5,916,911; 5,945,442; 5,952,370; 6,030,995; 6,040,332 and 6,051,598. Preferred compounds include but are not limited to PDMP and its derivatives, wherein PDMP is 1-phenyl-2-decanoylamino-3-morpholino-1-propanol (see U.S. Pat. No. 5,916,911) and P4 and its derivatives, wherein P4 is D-threo-1-phenyl-2-palmitoylamino-3-pyrrolidino-1-propanol (see Lee et al., 1999, id.). Preferred P4 derivatives include D-threo-4'-hydroxy-1-phenyl-2-palmitoylamino-3-pyrrolidino-1-propanol (4'-hydroxy-P4), D-threo-1-(3',4'-trimethylenedioxy)phenyl-2-palmitoylamino-3-pyrrolidino-1-propanol (trimethylenedioxy-P4), D-threo-1-(3',4'-methylenedioxy)phenyl-2-palmitoylamino-3-pyrrolidino-1-propanol (methylenedioxy-P4) and D-threo-1-(3',4'-ethylenedioxy)phenyl-2-palmitoylamino-3-pyrrolidino-1-propanol (ethylenedioxy-P4 or D-t-et-P4). An especially preferred P4 derivative is ethylenedioxy-P4 (see e.g. D-t-et-P4 in FIG. 1).

Preferred dosages of P4 derivatives including D-t-et-P4 in a combination therapy of the invention are easily determined by the skilled artisan. Such dosages may range from 0.5 mg/kg to 50 mg/kg, preferably from 1 mg/kg to 10 mg/kg by intraperitoneal or equivalent administration from one to five times daily. Such dosages may range from 5 mg/kg to 5 g/kg, preferably from 10 mg/kg to 1 g/kg by oral or equivalent administration from one to five times daily. A particularly preferred oral dose range for a P4-like compound is from 6 mg/kg/day to 600 mg/kg/day.

Deoxynojirimycin-like compounds and related small molecules are useful in the combination therapies of the invention. N-butyldeoxynojirimycin (NB-DNJ or OGT 918) and derivatives thereof are preferred in combination therapies of the invention for treatment of storage diseases in the glycosphingolipid pathway. The use of OGT 918 alone as an oral treatment for Gaucher's disease has been reported by Cox et al., 2000, Lancet 355, 1481-1485. OGT 918 can be used in combination therapies of the invention for any storage disease of the glycosphingolipid pathway, including Sandhoff and Tay-Sachs disease (see e.g. Jeyakumar et al., 2001, Blood 97, 327-329; Andersson et al., 2000, Biochem. Pharmacol. 59, 821-829; Jeyakumar et al., 1999, Proc. Natl. Acad. Sci. USA 96, 6388-6393; and Platt et al., 1997, Science 276, 428-431). Preferred deoxynojirimycin derivatives include but are not limited to N-propyldeoxynojirimycin, N-butyldeoxynojirimycin, N-butyldeoxygalactonojirimycin, N-pentlydeoxynojirimycin, N-heptyldeoxynojirimycin, N-pentanoyldeoxynojirimycin, N-(5-adamantane-1-ylmethoxy)pentyl)-deoxynojirimycin, N-(5-cholesteroxypentyl)-deoxynojirimycin, N-(4-adamantanemethanylcarboxy-1-oxo)-deoxynojirimycin, N-(4-adamantanylcarboxy-1-oxo)-deoxynojirimycin, N-(4-phenantrylcarboxy-1-oxo)-deoxynojirimycin, N-(4-cholesterylcarboxy-1-oxo)-deoxynojirimycin, or N-(4-p-cholestanylcarboxy-1-oxo)-deoxynojirimycin.

A particularly preferred deoxynojirimycin derivative for use in the combination therapies of the invention is N-(5-adamantane-1-yl-methoxy)pentyl)-deoxynojirimycin (AMP-DNJ or AMP-DNM, see FIG. 1). AMP-DNJ is among a variety of DNJ derivatives originally designed as research tools to aid in the elucidation of the physiological relevance of the non-lysosomal glucosylceramidase (Overkleeft et al., 1998, J. Biol. Chem. 273, 26522-26527). Another particularly preferred deoxynojirimycin derivative for use in the combination therapies of the invention is N-butyldeoxygalactonojirimycin (NB-DGJ), a DNJ-type inhibitor with greater selectivity (see Andersson et al., 2000, Biochem. Pharmacol. 59, 821-829).

Preferred dosages of DNJ derivatives including NB-DNJ, NB-DGJ, AMP-DNJ in a combination therapy of the invention are also readily determined by the skilled artisan. Such dosages may range from 0.01 mg/kg to 1000 mg/kg, preferably from 0.1 mg/kg to 100 mg/kg, more preferably from 1 mg/kg to 10 mg/kg, by intraperitoneal or equivalent administration from one to five times daily. Such dosages, when administered orally, may range from two- to twenty-fold greater. For example, OGT 918 (a.k.a. NB-DNJ) has been administered orally to humans in a 100 mg dose three times per day for twelve months, and a daily dose of up to 3 gm has been used. A particularly preferred oral dose range for a DNJ-like compound is from 60 mg/kg/day to 900 mg/kg/day.

The aminoglycosides such as gentamicin and G418 are particularly useful in the combination therapies of the invention where the affected individual has a storage disease with at least one allele comprising a premature stop-codon mutation. This approach is particularly useful in some Hurler syndrome patient populations, where premature stop mutations represent roughly two-thirds of the disease-causing mutations. The work by Bedwell and coworkers provides guidance for the skilled artisan in the use of stop-mutation suppressors such as the aminoglycosides (U.S. Pat. No. 5,840,702). Aminoglycoside-induced read-through of Hurler syndrome mutations have been described by Keeling et al., 2001, Hum. Molec. Genet. 10, 291-299. Some aminoglycosides which are preferred for use in the combination therapies of the invention include but are not limited to gentamicin, G418, hygromycin B, paromomycin, tobramycin and Lividomycin A.

Preferred dosages of aminoglycoside derivatives including gentamicin and G418 in a combination therapy of the invention are also readily determined by the skilled artisan. Such dosages may range from 1 mg/kg to 1000 mg/kg, preferably from 10 mg/kg to 100 mg/kg, more preferably from 5 mg/kg to 50 mg/kg, by intraperitoneal or equivalent administration from one to five times daily. Such dosages, when administered orally, may range from two- to twenty-fold greater.

Any storage disease resulting at least in part from a premature stop codon can be treated with an aminoglycoside in combination with GT and/or ERT. A number of examples of storage diseases for which premature stop codons have been identified are provided in the following references: Peltola et al., 1994, Hum. Molec. Genet. 3, 2237-2242 (Aspartylglucosaminuria); Voskoboeva et al., 1994, Hum. Genet. 93, 259-64 (Maroteaux-Lamy); Yang et al., 1993, Biochim. Biophys. Acta 1182, 245-9 (Fucosidosis); Takahashi et al., 1992, J. Biol. Chem. 267, 12552-8 (Niemann-Pick); Beutler et al., 1996, Proc. Assoc. Am. Phys. 108, 179-84 (Gaucher); Hara et al., 1994, Hum. Genet. 94, 136-40 (Sandhoff); Zhang et al., 1994, Hum. Molec. Genet. 3, 139-145 (Sandhoff); Tanaka et al., 1999, J. Hum. Genet. 44, 91-5 (Tay-Sachs); Okumiya et al., 1996, Jpn. J. Hum. Genet. 41, 313-21 (Fabry); Drucker et al., 1993, Hum. Mutat. 2, 415-7 (Tay-Sachs); and Sakuraba et al., 1990, Am. J. Hum. Genet. 47, 784-9 (Fabry). To determine whether a storage disease individual will benefit from a combination therapy which includes an aminoglycoside (or any other agent able to elicit read-through), the clinician simply has the individual genotyped to determine whether a premature stop codon mutation is present in one or more disease alleles.

5.12 Dosing Regimens & Other Considerations

Initially, gene therapy is preferred to debulk accumulated lysosomal storage material in affected cells and organs. However, expression from currently-available gene therapy vectors generally extinguishes over time. Accordingly, gene therapy may be followed with recombinant enzyme administration when gene expression begins to decline. ERT may be continued, for example, until the antibody titer against the viral vector being used has abated sufficiently to allow re-dosing with gene therapy. Switching to a different gene therapy vector is also possible. Finally, both the GT and ERT phases of treatment may be supplemented with SMT, as needed, depending on the clinical course of a given storage disease in a given individual.

Alternatively, as expression from a gene therapy vector extinguishes over time, GT may be followed with substrate inhibition therapy (using one or more small molecules) to abate the rate of re-accumulation of storage material. Depending on the rate of re-accumulation, patients can be re-treated with gene therapy (when immune status indicators indicate it is safe to do so) or with enzyme therapy. The intervening period between gene therapy and substrate inhibition and/or enzyme therapy is dictated by storage disease type and severity. Individuals which have lysosomal storage disorders that accumulate storage material slowly over time, or those which have relatively high levels of residual enzyme activity, will require less-frequent re-treatment with gene therapy at longer intervals.

Enzyme therapy can also be used initially to debulk accumulated lysosomal storage in affected cells and organs. After debulking, subjects may receive substrate inhibition therapy to abate the rate of re-accumulation of storage material in affected lysosomes. The re-accumulation rate will vary, depending on disease type and severity, and subjects can subsequently receive re-treatment with enzyme therapy, or with gene therapy, as needed as determined by the skilled clinician.

After enzyme therapy debulking, subjects may alternatively be treated with gene therapy which could provide therapeutic levels of enzyme for several months. As expression expires, subjects may return to enzyme therapy or receive substrate inhibition therapy.

A rotating combination of two of the three therapeutic platforms (i.e. gene, enzyme and substrate inhibition therapy) is preferred. However, subjects may also be treated by rotating (or overlapping) all three approaches as needed, as determined by the skilled clinician. Examples of treatment schedules may include but are not limited to: (1) gene therapy, then substrate inhibition followed by enzyme therapy; (2) enzyme therapy, then substrate inhibition followed by gene therapy; (3) gene therapy, then enzyme therapy followed by substrate inhibition therapy; (4) enzyme therapy, then gene therapy followed by substrate inhibition therapy. As noted previously, temporal overlap of therapeutic platforms may also be performed, as needed, depending on the clinical course of a given storage disease in a given subject.

A substrate inhibition component to a combination therapy is conceptually applicable to virtually all lysosomal storage disorders. LSDs amenable to treatment by substrate inhibition with DNJ and P4 type molecules include those of the glycosphingolipid pathway (e.g. Gaucher, Fabry, Tay-Sachs, Sandhoff and $G_{M1}$-gangliosidosis).

The various macromolecules that accumulate in lysosomal storage diseases are not uniformly distributed, but instead are deposited in certain preferred anatomic sites for each disease. However, an exogenously supplied enzyme, whether delivered by enzyme replacement therapy or gene therapy, is generally taken up by cells of the reticuloendothelial system and sorted to the lysosomal compartment where it acts to hydrolyze the accumulated substrate. Moreover, cellular uptake of therapeutic enzyme can be augmented by certain maneuvers to increase lysosomal targeting (see e.g. U.S. Pat. No. 5,549,892 by Friedman et al., assigned to Genzyme Corporation, which describes recombinant glucocerebrosidase having improved pharmacokinetics by virtue of remodeled oligosaccharide side chains recognized by cell surface mannose receptors which are endocytosed and transported to lysosomes).

Treatment intervals for various combination therapies can vary widely and may generally be different among different storage diseases and different individuals depending on how aggressively storage products are accumulated. For example, Fabry storage product accumulation may be slow compared to rapid storage product accumulation in Pompe. Titration of a particular storage disease in a particular individual is carried out by the skilled artisan by monitoring the clinical signs of disease progression and treatment success.

Some treatment modalities target some affected organs better than others. In Fabry, if ET does not reach the kidney well enough for a satisfactory clinical outcome, GT can be selectively targeted to the kidney (e.g., by injection). Other organs or disease loci such as bones and lung alveolar macrophages may not be well targeted by ET. Using GT, however, bones can be injected and lungs can be targeted with aerosols. SMT is able to cross the BBB, providing a powerful approach, when combined with GT and/or ERT, for treating LSDs having CNS manifestations. Moreover, substrate deprivation by SMT combined with enzyme replacement and/or gene therapy address the storage problem at separate and distinct intervention points which may enhance clinical outcome.

It will be understood that reference to simultaneous or concurrent dministration of two or more therapies does not require that they be administered at the ame time, just that they be acting in the subject at the same time.

6. EXAMPLE

Fabry mice were used to test the in vivo efficacy of combining enzyme eplacement therapy with small molecule therapy in a sequential treatment format (FIG. 1). The study was designed to evaluate whether substrate inhibition (i.e. "substrate deprivation herapy") using small molecules of the DNJ and P4 types could reduce re-accumulation of the storage material globotriaosylceramide (GB3). The study protocol (FIG. 1A) called for a single infusion of a-galactosidase A enzyme to reduce GB3 levels (measured at two weeks) to a "Baseline" level in Fabry mouse liver. GB3 re-accumulation was then measured at four weeks in control mice receiving no small molecule therapy ("Vehicle") and in mice receiving various small molecules at various doses. Accordingly, two weeks after GB3 levels were reduced to a "Baseline" level of about 0.1 μg/g liver (FIG. 1B), a small molecule or vehicle was administered by intra-peritoneal (IP) injection. In the vehicle-treated control mice, GB3 re-accumulated to about 0.8 μg/gm liver tissue at the four week time point. By contrast, D-t-et-P4 (5 mg/kg) reduced GB3 re-accumulation to less than 0.4 μg/gm liver tissue at the four week time point. Similarly, AMP-DNJ (100 mg/kg) reduced GB3 re-accumulation to less than 0.3 μg/gm liver tissue at the four week time point. These results demonstrate the effectiveness of combination therapy in a storage disease mouse model. Specifically, small molecule therapy reduced the re-accumulation of storage material following its reduction by enzyme replacement therapy. These results also demonstrate the unexpected benefit of combining a hydrophobic DNJ derivative (i.e. AMP-DNJ) designed as a research tool for selective inhibition of a non-lysosomal enzyme (see (Overkleeft et al., 1998, J. Biol. Chem. 273, 26522-26527) with enzyme replacement.

The invention described and claimed herein is not to be limited in scope by the specific embodiments herein disclosed, since these embodiments are intended only as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated-by-reference into the present application in its entirety.

What is claimed is:

1. A method of reducing the levels of globotriaosylceramide in a patient, comprising the steps of:
    a) administering a therapeutically effective amount of an α galactosidase to debulk accumulated lysosomal globotriaosylceramide in the patient; and
    b) administering a small molecule chosen from a D-threo-1-phenyl-2-palmitoylamino-3-pyrrolidino-1-propanol (P4) and a P4 derivative to reduce the rate of re-accumulation of the lysosomal globotriaosylceramide,
    wherein step (b) begins about two weeks after step (a).

2. The method of claim 1, wherein the α galactosidase is administered by infusion.

3. The method of claim 1, where in the small molecule is administered for at least two weeks.

* * * * *